United States Patent [19]

Shturman

[11] Patent Number: 5,221,258
[45] Date of Patent: Jun. 22, 1993

[54] INTRODUCTION BALLOON CATHETER

[75] Inventor: Leonid Shturman, Minneapolis, Minn.

[73] Assignee: Shturman Technologies, Inc., Minneapolis, Minn.

[21] Appl. No.: 643,919

[22] Filed: Jan. 22, 1991

[51] Int. Cl.$^5$ .............................................. A61M 25/00
[52] U.S. Cl. ...................................... 604/96; 609/192; 128/4; 128/6; 604/280
[58] Field of Search .................................. 604/95–101, 604/158, 161, 163, 164, 171, 280, 284; 128/4, 6, 656–658, 772; 606/191, 192, 194

[56] References Cited

U.S. PATENT DOCUMENTS

| | | | |
|---|---|---|---|
| 4,517,979 | 5/1985 | Pecenka | 604/99 |
| 4,867,742 | 9/1989 | Calderon | 604/101 |
| 4,886,062 | 12/1989 | Wiktor | 604/194 |
| 4,911,163 | 3/1990 | Fina | 604/101 |
| 4,946,440 | 8/1990 | Hall | 604/97 |
| 4,960,411 | 10/1990 | Buchbinder | 604/96 |
| 5,000,743 | 3/1991 | Patel | 604/101 |
| 5,002,558 | 3/1991 | Klein et al. | 604/101 |
| 5,021,045 | 6/1991 | Buckberg et al. | 604/96 |
| 5,024,658 | 6/1991 | Kozlov et al. | 604/101 |
| 5,078,681 | 1/1992 | Kawashima | 604/96 |

FOREIGN PATENT DOCUMENTS

| | | | |
|---|---|---|---|
| 0359447 | 3/1990 | European Pat. Off. | 604/96 |
| 2647681 | 12/1990 | France | 606/194 |
| 0177124 | 9/1986 | Japan | 604/97 |
| 1251914 | 8/1986 | U.S.S.R. | 606/194 |

OTHER PUBLICATIONS

Palmaz, J. C., et al., "Normal and Stenotic Renal Arteries: Experimental Balloon–expandable Intraluminal Stenting," *Radiology*, vol. 164, No. 3, pp. 705–708, Sep. 1987.

Palmaz, J. C., et al., "Intraluminal Stents in Atherosclerotic Iliac Artery Stenosis: Preliminary Report of a Multicenter Study," *Radiology*, vol. 168, No. 3, pp. 727–731, Sep. 1988.

Rutan, P. M., et al., "Initial Experience with the Hemopump," *Critical Care Nursing Clinics of North America*, vol. 1, No. 3, pp. 527–534, Sep. 1989.

Frazier, O. H., et al., "First Human Use of the Hemopump, a Catheter-Mounted Ventricular Assist Device," *Ann. Thorac. Surg.*, 1990:49:299–304.

Shawl, Fayaz A., et al., "Percutaneous Cardiopulmonary Bypass Support in the Cathertization Laboratory: Technique and Complications," *American Heart Journal*, vol. 120, No. 1, Jul. 1990, pp. 195–203.

*Primary Examiner*—C. Fred Rosenbaum
*Assistant Examiner*—Charles Smith
*Attorney, Agent, or Firm*—Gregory P. Kaihoi

[57] ABSTRACT

Apparatus and method for delivering over-sized or large bore devices through passageways in the body. The apparatus comprises an elongated inflatable balloon having an inner diameter slightly larger than the outer diameter of the device to be introduced into the passageway. A guidewire may be utilized to assist introduction of the balloon into the bodily passageway. A device introduction chamber is attached at the proximal end of the balloon for temporarily housing the device being introduced into the passageway, and the device itself includes a delivery shaft at least partially disposed in the introduction chamber. An inflation device is provided for inflating the balloon with a biologically compatible fluid once the balloon has been inserted into the bodily passageway. The distal portion of the balloon is inserted into the bodily passageway, the balloon is then inflated to expand and straighten the passageway, and the device may then be advanced through the balloon into the passageway. The invention is particularly useful for introducing over-sized devices through smaller, secondary passageways into larger, primary passageways, such as through the femoral artery into the aorta. After the device has been advanced within the balloon into the larger, primary passageway, the balloon may be ruptured to free the device from the balloon, allowing to the device to be further advanced through the passageway to a destination such as the heart.

32 Claims, 28 Drawing Sheets

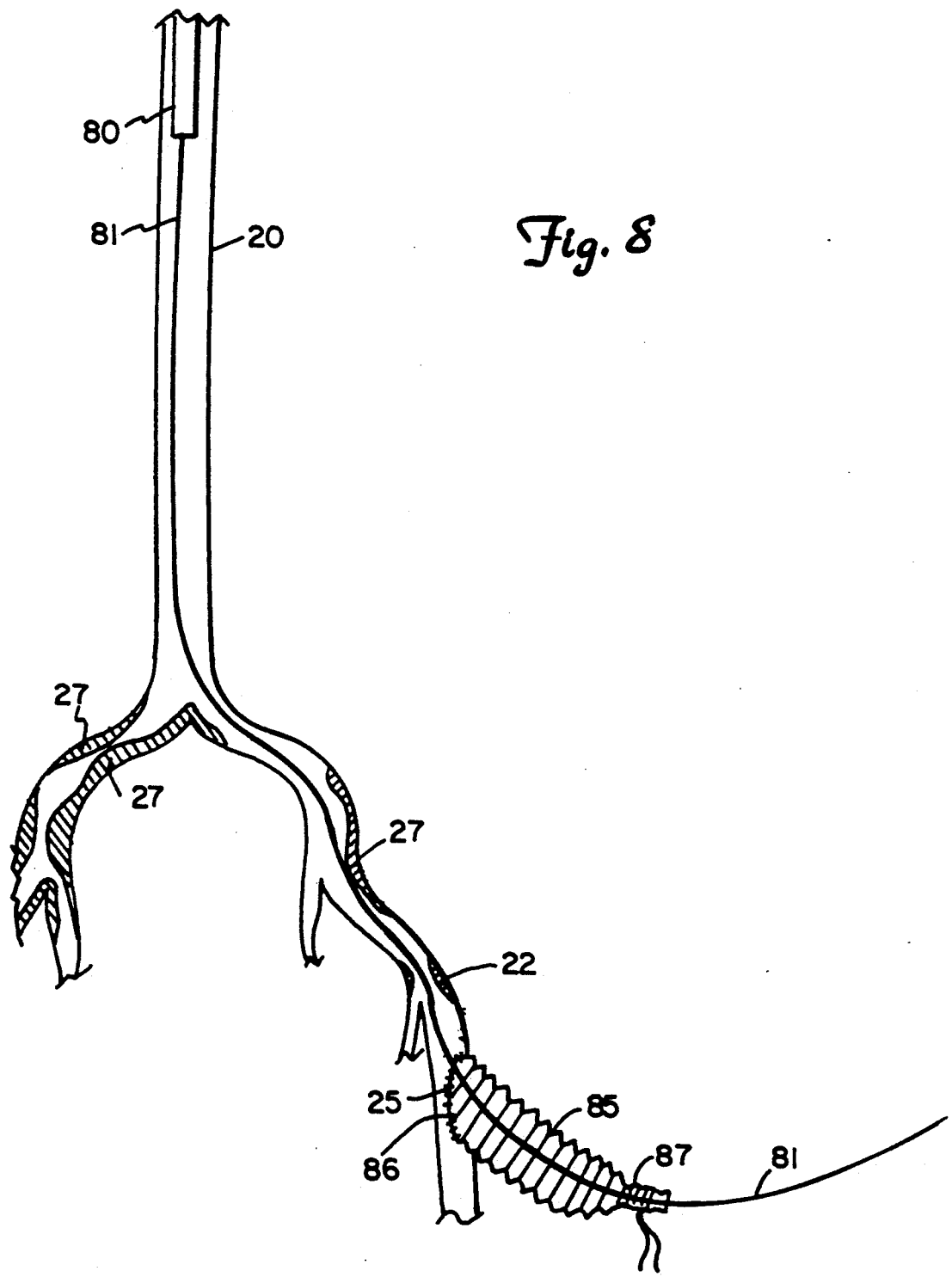

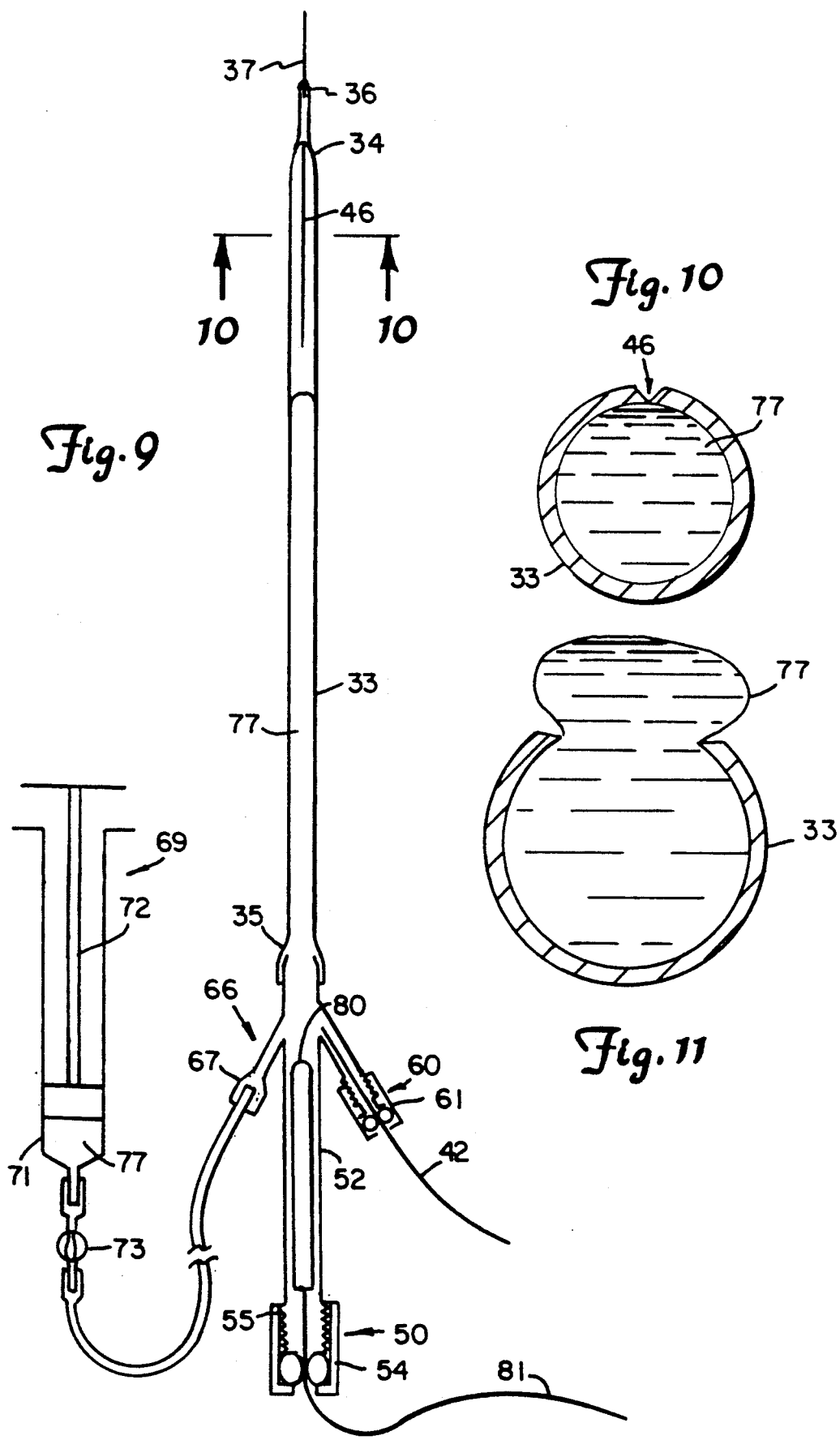

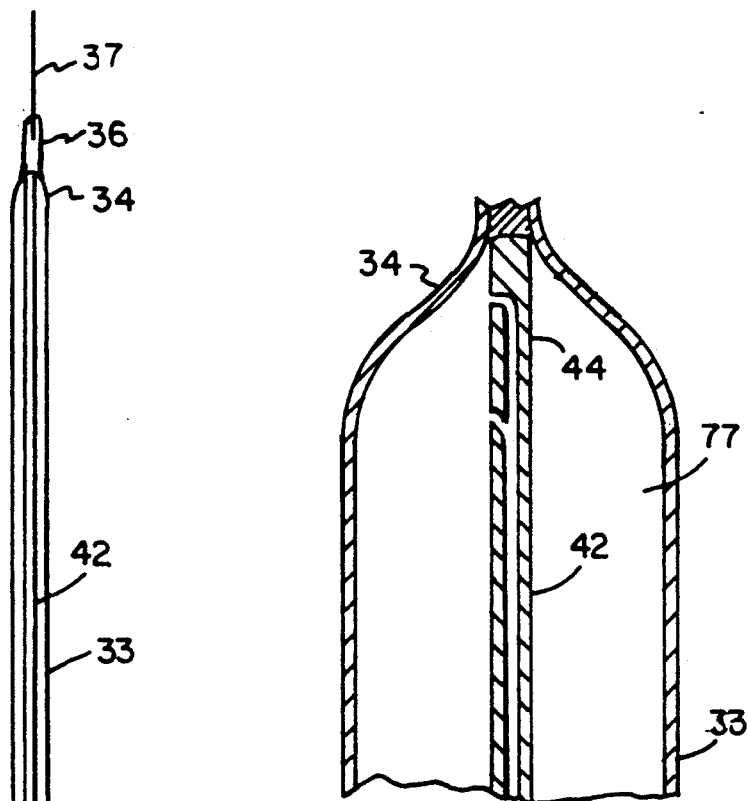
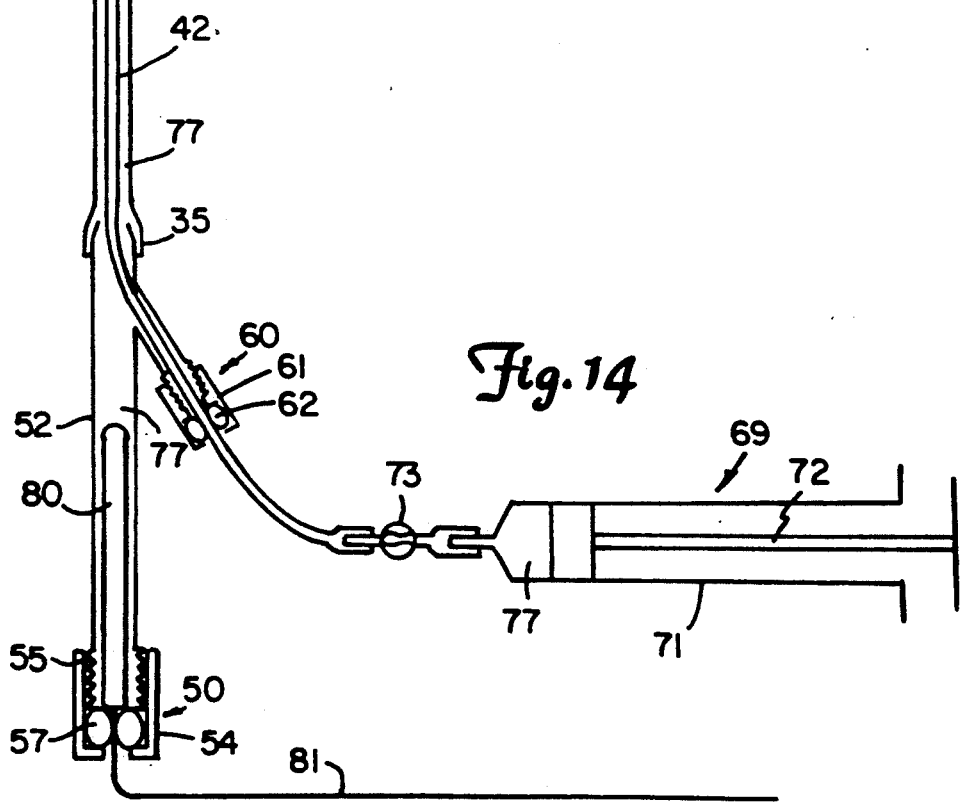
Fig. 14A
Fig. 14

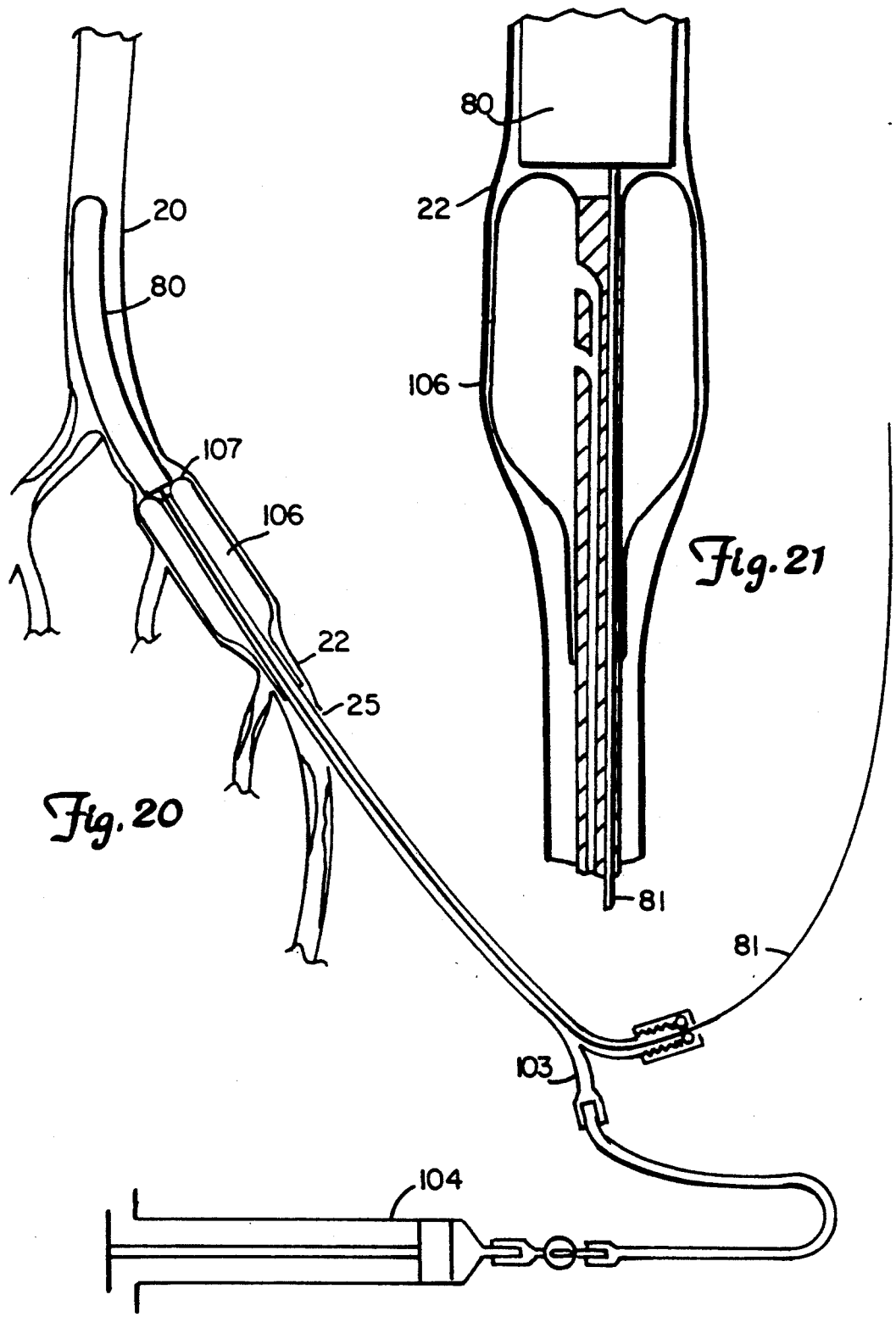

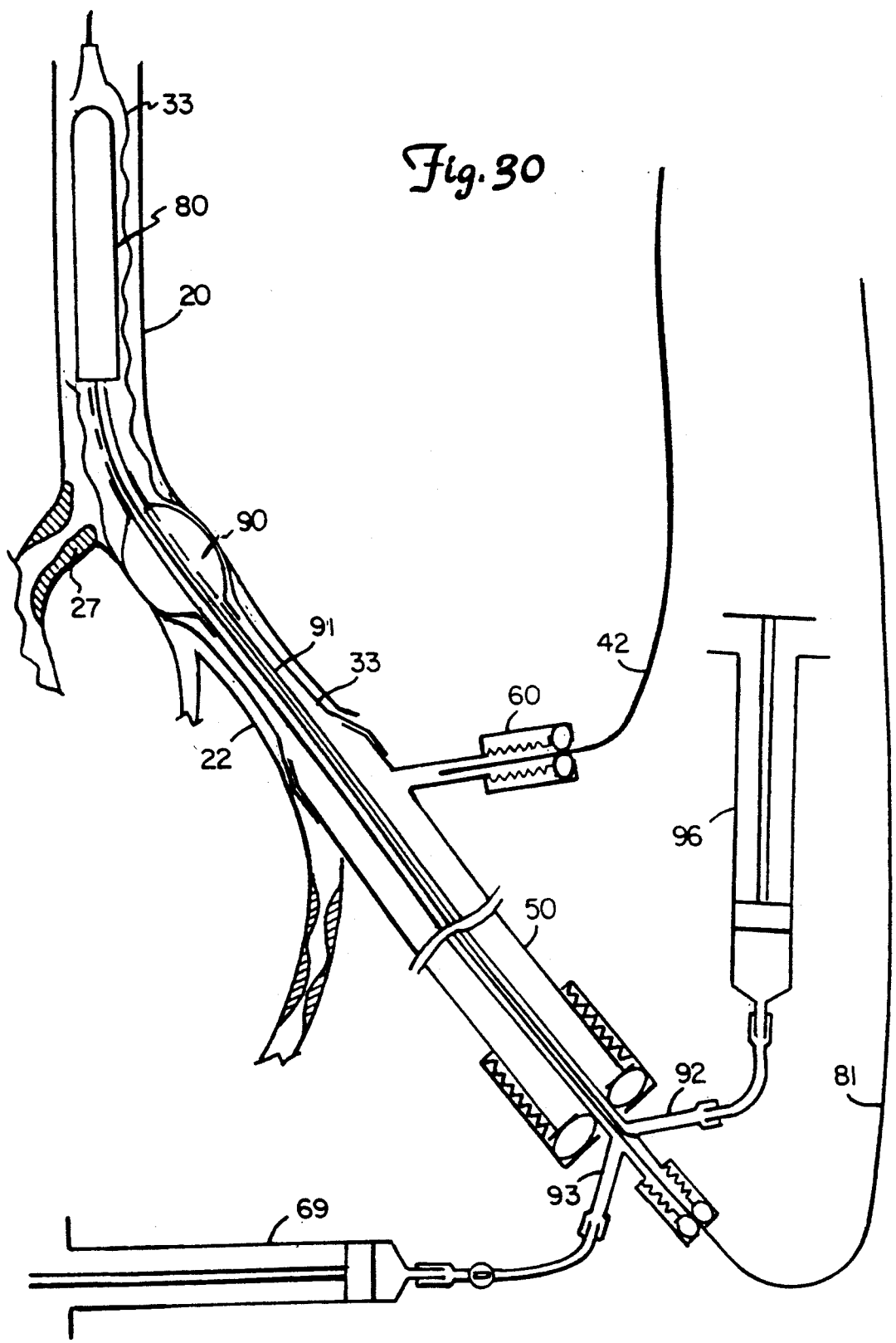

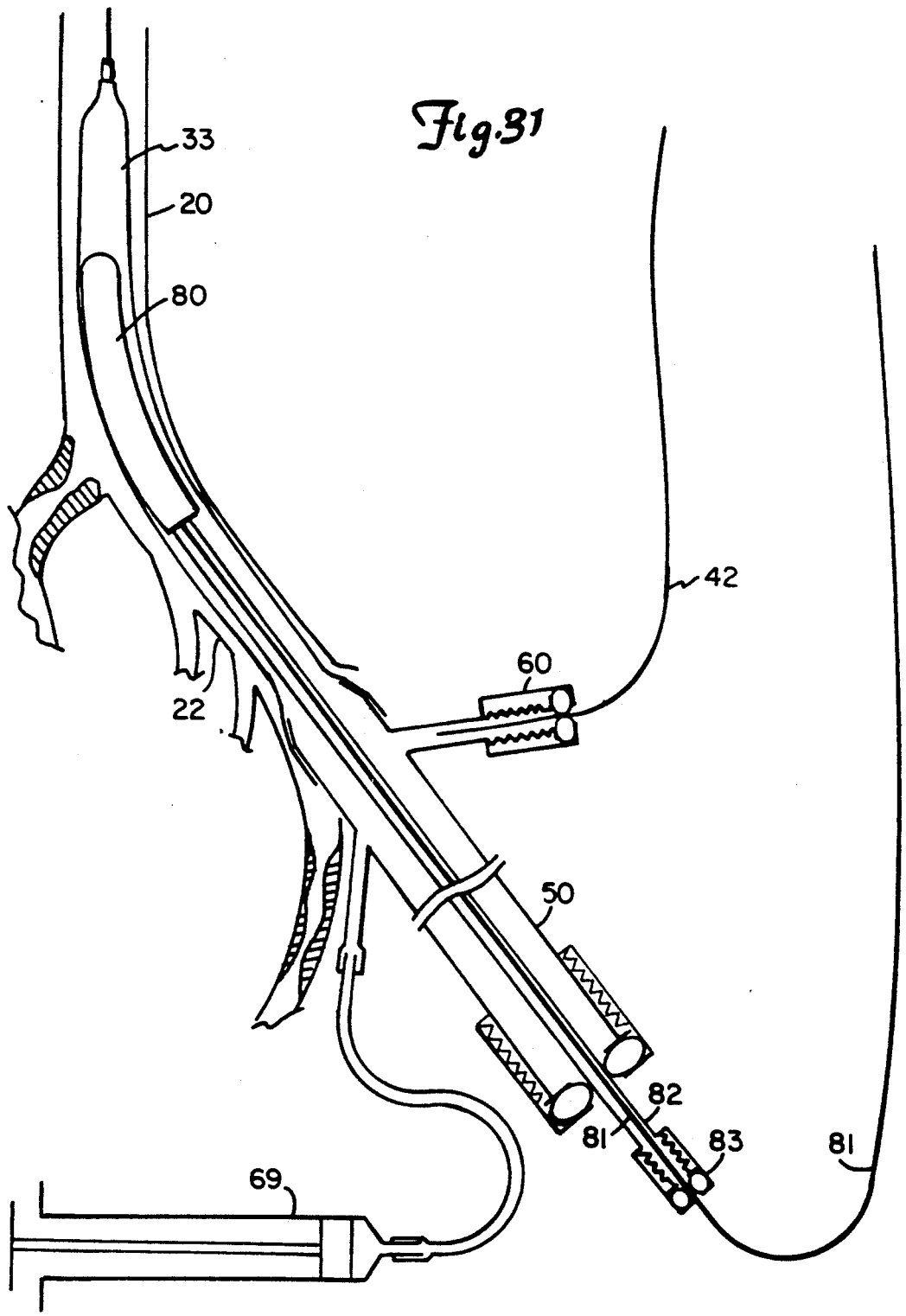

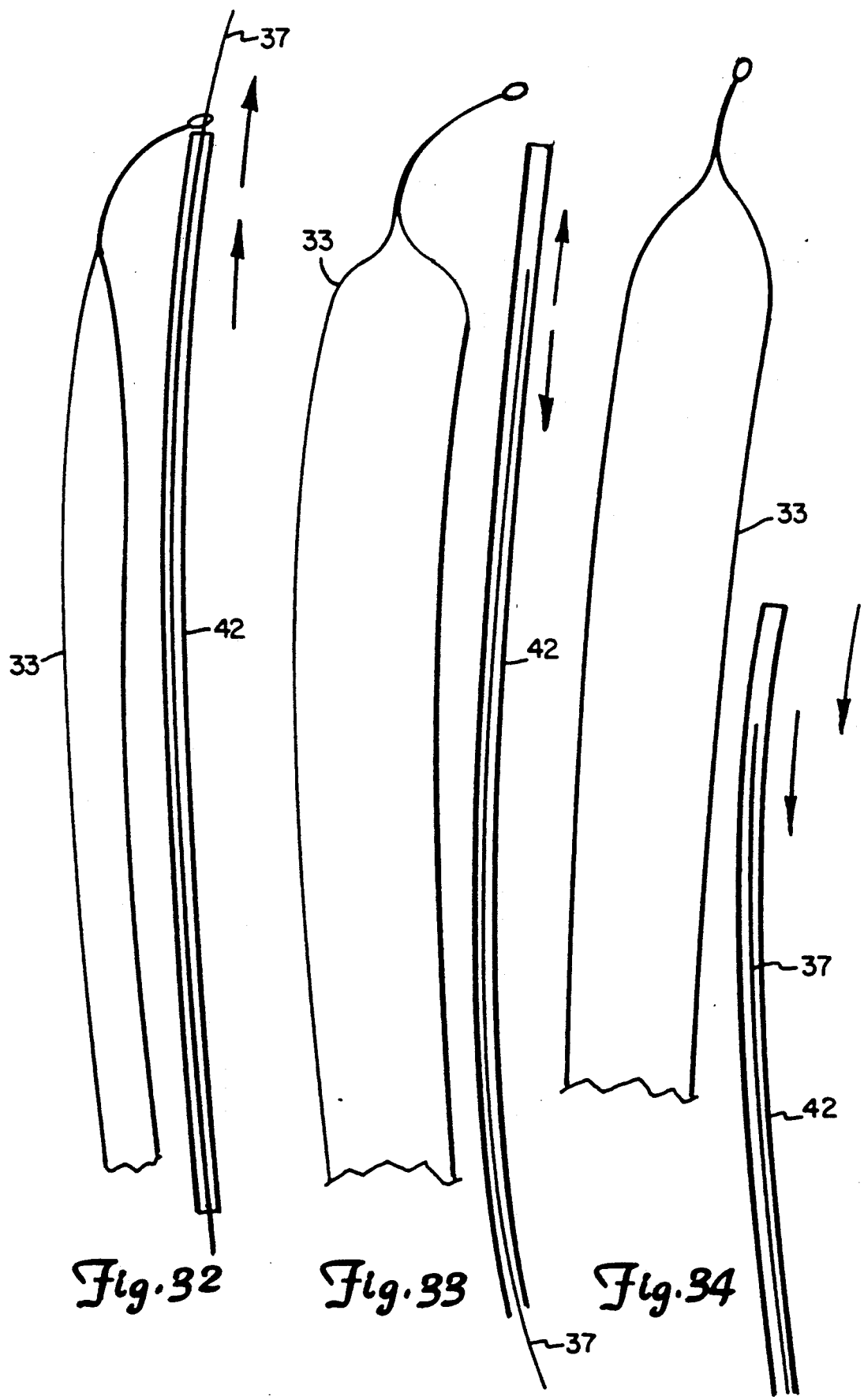

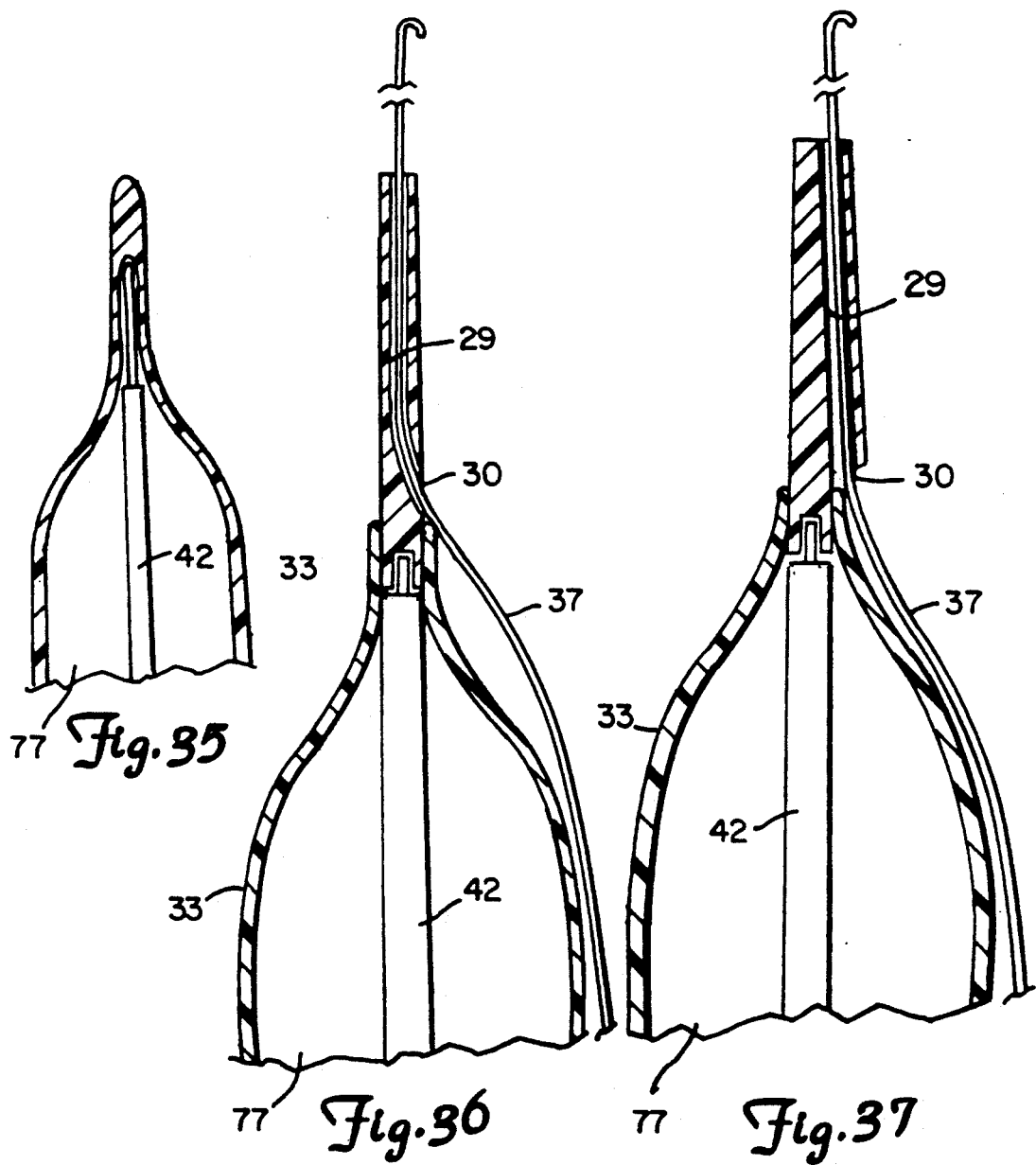

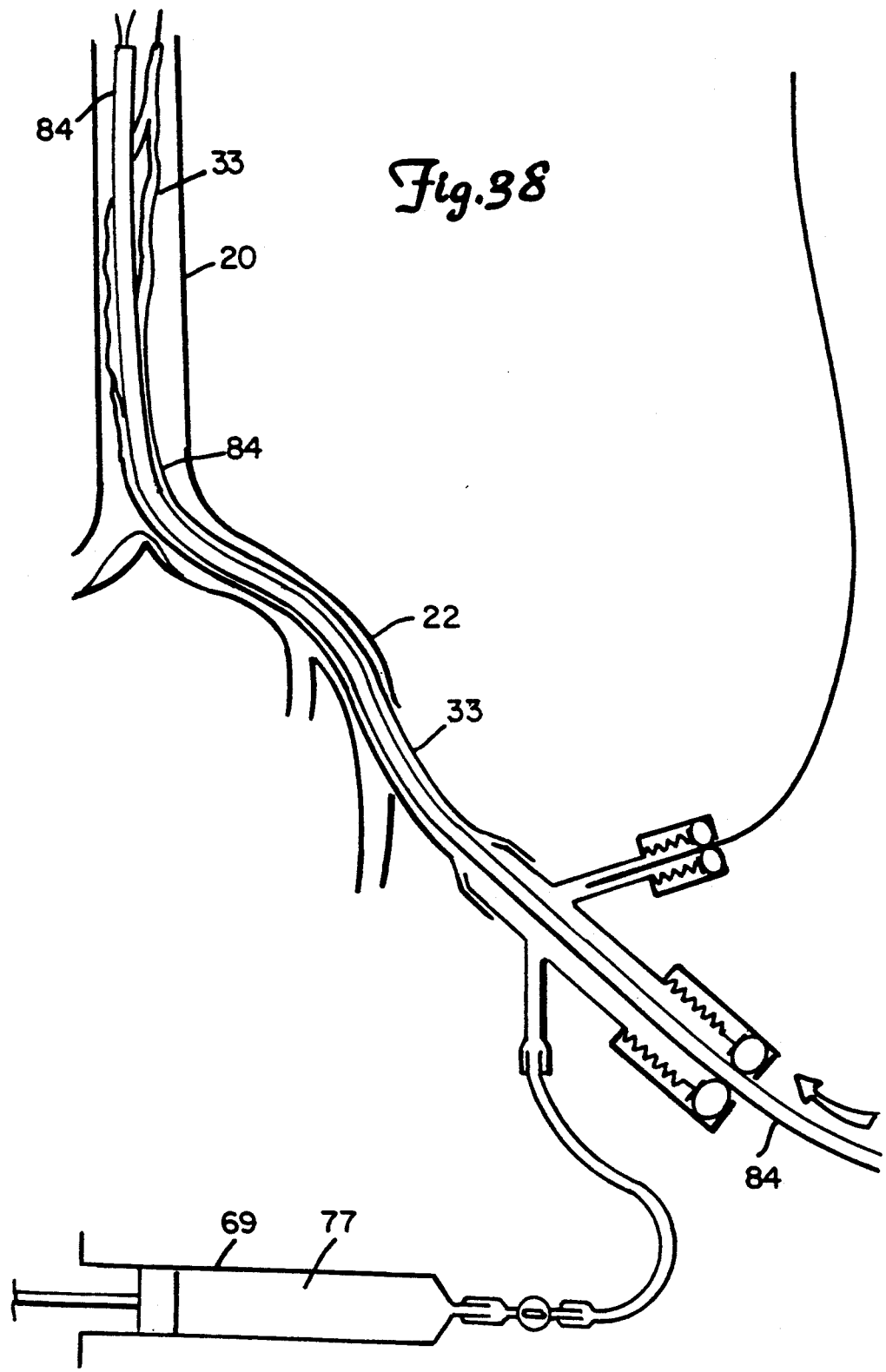

INTRODUCTION BALLOON CATHETER

TECHNICAL FIELD

The invention relates to catheters for use in bodily passageways, and more particularly to a balloon catheter usable to introduce over-sized or large-bore objects into restricted passageways in the body, such as veins or arteries and the like, and particularly into atherosclerotic arteries.

BACKGROUND OF THE INVENTION

Catheterization of vascular and other passageways in the body is a well known technique used to accomplish a variety of tasks, including draining fluids from the body, introducing fluids (such as imaging fluids) into the passageways, performing repair procedures (such as angioplasty) and so forth.

The uses and desired uses of catheters is ever growing, owing at least in part to the attractiveness of being able to accomplish certain invasive tasks that otherwise would require surgery or sometimes even open heart surgery. Catheter procedures in lieu of surgery typically are less traumatic to the patient, and often reduce or eliminate many of the risks associated with surgery. Moreover, catheter procedures usually are much cheaper than surgery, if for no other reason that in-hospital recovery time is often significantly reduced or eliminated.

For example, as an alternative to cardiac coronary artery bypass surgery, balloon catheters have been used in coronary angioplasty for opening narrowed (atherosclerotic) coronary arteries. In such a procedure, a guidewire is advanced into the artery, followed by a balloon catheter. When a section of the artery is encountered that has been narrowed by plaque deposits (a stenosis or lesion) the balloon is properly positioned (as determined by conventional radiological imaging) and then inflated. The balloon dilates the narrowed section of the artery, compressing the plaque and slightly stretching the artery to widen the blood passageway. The balloon is then deflated, and may be advanced to another stenosis, or removed upon completion of the desired procedure. Detailed descriptions of such procedures may be found in, e.g., G. Jang. *Angioplasty* (1986).

Beyond angioplasty, catheters are also useful for providing a secure passageway through which small devices may be delivered to remote locations in the body. There are many desired uses for such catheters, however, that heretofore have been impossible or impractical due to the size of the device desired to be delivered through a passageway. The size of such devices is necessarily limited by the internal diameter of the catheter, and the size of the catheter in turn is limited by the internal diameter (and other factors, such as tortuosity, atherosclerotic plague, etc.) of the passageway itself.

This problem is compounded by the fact that often the patient needing a particular procedure may be advanced in age, which often means that the passageway may be somewhat more tortuous than in a younger patient. Moreover, in the case of arteries, the atherosclerotic process may have irregularly narrowed the arteries with artheroscelrotic plagues.

SUMMARY OF THE INVENTION

The invention provides an apparatus and method for delivering otherwise oversized devices through passageways in the body. The apparatus comprises an elongated inflatable balloon having an inner diameter slightly larger than the outer diameter of the device to be introduced into the passageway. A guidewire may be attached to the distal end of the balloon to assist introduction of the balloon into the bodily passageway. A device introduction chamber is attached at the proximal end of the balloon for temporarily housing the device being introduced into the passageway, and the device itself includes a delivery shaft at least partially disposed in the introduction chamber. Inflation means is provided for inflating the balloon once the balloon has been inserted into the bodily passageway.

The device is particularly useful in traversing narrowed portions of a bodily passageway, such as introducing a device through the narrowed (particularly atherosclerotically narrowed) femoral artery into the wider abdominal aorta. The method therefore comprises the steps of inserting at least the distal portion of the uninflated balloon into the bodily passageway (preferably advancing at least the distal end past the narrowed portion of the passageway that must be traversed), inflating the balloon to expand and straighten (if necessary) the passageway, and then advancing the device from the introduction chamber into the distal portion of the balloon.

In a preferred embodiment, the balloon is configured so that the device can be freed from the balloon. Preferably this is accomplished by configuring the balloon so that it can be ruptured near its distal end to free the device, allowing the device to be advanced through the wider passageway to its destination (such as advancing through the aorta to the heart). Such rupture may be accomplished through any suitable means. Preferably the rupture in the balloon is longitudinally oriented, and thus, in a particularly preferred embodiment, the balloon includes a longitudinal weakness so that upon over-inflation of the balloon the balloon will rupture along the longitudinal weakness. Alternately, the balloon may include a distal portion that is of a larger diameter than the rest of the balloon so that upon over-inflation a longitudinal rupture will occur in the distal, larger portion.

To stiffen the uninflated balloon catheter for insertion into, the passageway, the balloon catheter desirably includes a shaft engaged at its distal end to the distal end of the balloon. The shaft preferably is removable by disengaging it from the distal end of the balloon (as by unscrewing threads or merely pulling it loose from a friction fit or retracting it from a nonfriction site of engagement) and withdrawing it through a port in the introduction chamber to allow the device to be advanced into the balloon without interference from the shaft.

BRIEF DESCRIPTION OF THE DRAWINGS

FIG. 8 shows placement of a prosthetic vascular graft attached to the vascular entry wound, tied off around the delivery shaft to prevent blood leakage;

FIG. 9 shows an introduction balloon catheter of the invention having a balloon with a longitudinally weakened portion near its distal end;

FIG. 10 is a cross-sectional view of FIG. 9 taken along line 10—10 thereof;

FIG. 11 is a cross-sectional view similar to FIG. 10 but after the balloon has ruptured;

FIG. 14 shows an introduction balloon catheter of the invention wherein the balloon shaft comprises a catheter through which inflation fluid may be delivered;

FIG. 14A in an enlarged view of the distal end of the catheter of FIG. 14;

FIGS. 20-21 show another removal balloon catheter similar in function to the removal balloon catheter of FIG. 19;

FIG. 30 shows an alternate embodiment similar to FIGS. 27-29;

FIG. 31 shows an alternate embodiment of the introduction balloon catheter of the invention having an additional stiffening shaft about the device delivery shaft;

FIGS. 32-34 show an alternate embodiment wherein the balloon shaft is positioned external to the balloon;

FIG. 35 shows the distal end of an alternate embodiment of the invention that does not utilize a guidewire;

FIGS. 36-37 show alternate embodiments that include additional means for utilizing a guidewire with the balloon introduction catheter of the invention; and FIGS. 38-39 depict a method of using the balloon introduction catheter of the invention to insert and remove a large bore catheter or cannular from an artery.

BEST MODE FOR CARRYING OUT THE INVENTION

Figure 1:
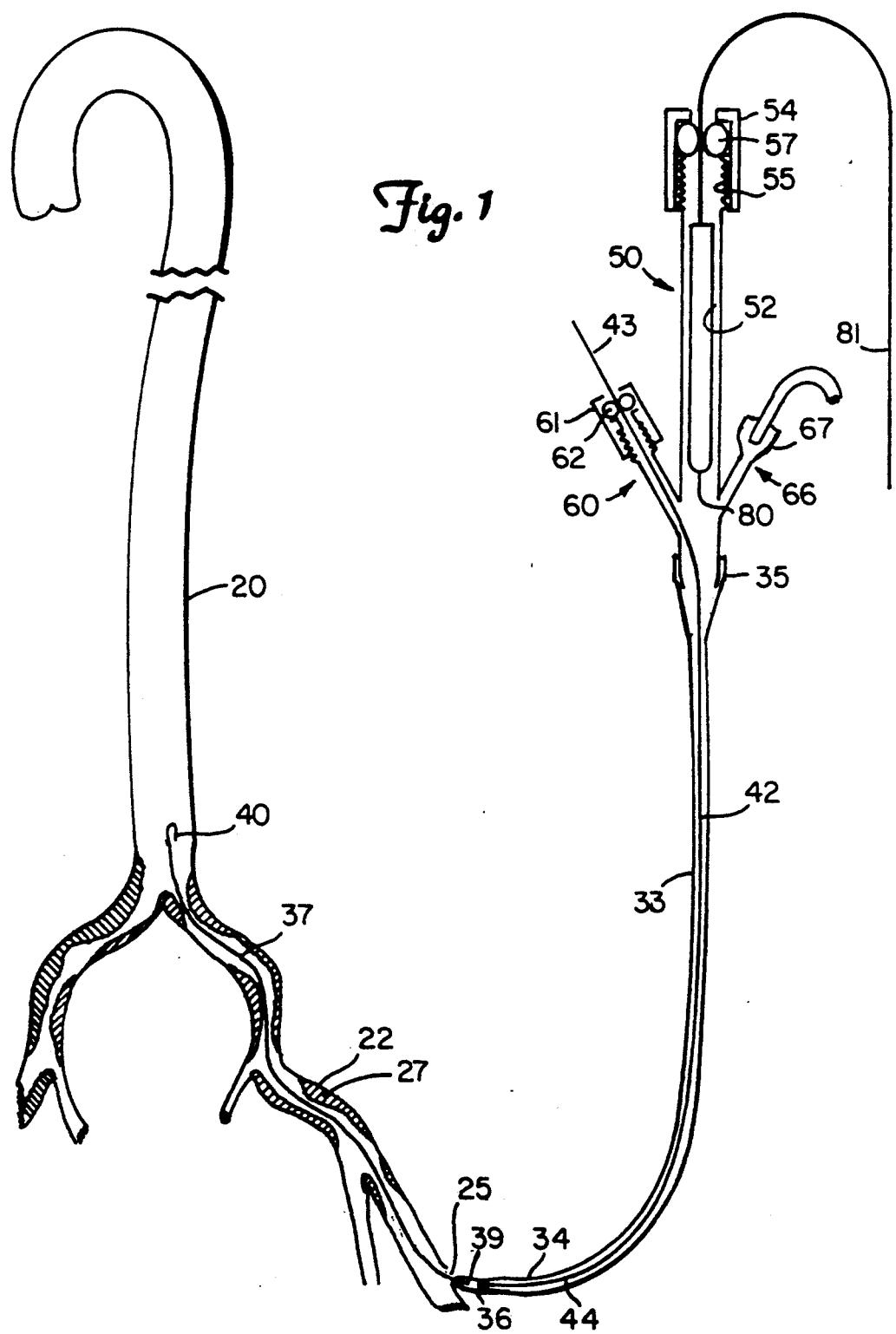
FIG. 1 shows an introduction balloon catheter of the invention with the guidewire inserted into the femoral artery, through the iliac artery, with the distal end entering the abdominal aorta.

FIGS. 1-7 depict the series of steps involved in utilizing the introduction balloon cathter of the invention. The introduction balloon catheter is usable in a variety of bodily passageways, including but not limited to the vascular system, the urinary system, the digestive system, and the like. It is particularly useful for introducing devices of a diameter large enough that insertion with conventional introducers, sheaths or catheters is difficult or impossible. Typically, this will occur when the device (80) is of a diameter larger than, equal to, or approaching the diameter of the passageway.

The introduction balloon catheter of the invention is particularly useful when the passageway may be partially occluded, such as by atherosclerotic plaque, and when the passageway is somewhat tortuous, as is often the case in elderly patients. Moreover, the invention is particularly useful when the deivce is being introduced through a passageway that is narrow along a part of its path, but then widens, as in the case of introducing devices through the femoral artery to the aorta (and then to the heart itself), or, e.g., through the urethra to the bladder or past any partial blockage in a passageway. For purposes of illustrating use of the invention, the drawings depict use of the invention for advancing a device (80) through the femoral and iliac arteris (22) into the abdominal aorta (20). (Artery (22) is herein frequently referred to as the femoral artery, but it should be understood that the portion of this artery adjacent to the aorta is called the iliac, and references herein to the femoral artery usually are equally applicable to the iliac portion of this artery.)

The introduction balloon catheter of the invention includes an elongated balloon (33) having a distal end (34) and a proximal end (35). A guidewire (37) desirably is attached at its proximal end (39) to the distal end (34) of the balloon (33) (though, as described below, other configurations are also possible). The distal end (40) of the guidewire (37) may be straight, may include a safety J-tip, or be of any other suitable configuration.

The proximal end (35) of the balloon (33) is attached to an introduction chamber (50), which temporaily houses the device (80) to be introduced into the artery. The introduction chamber (50) includes a main chamber portion (52), which houses the device (80), and may include one or more additional ports. In the preferred embodiment shown in FIGS. 1-5, the introduction chamber (50) includes two additional ports. A fluid port (66) is provided to facilitate inflation of the balloon by injection of a fluid (77), and a balloon shaft port (60) is also provided to facilitate removal of the balloon shaft (42), as described in greater detail below. The main chamber (52) and the balloon shaft port (60) of the introduction chamber (50) both include threaded compression fittings (54) and (61), respectively, with sealing rings (57) and (62), respectively, for allowing insertion and/or withdrawal of the device delivery shaft (81) and balloon shaft (42), as desired. These fittings mayb e tightened against their respective sealing rings to prevent excessive escape of fluid (77), and also may be loosened to facilitate easier advancement or retraction of the shaft (81) and shaft (42).

An inflation device (69) is attached to the fluid port (66) by a suitable fitting (67). The inflation device typically comprises a syringe (71) having a plunger (72) for injecting a fluid to inflate the balloon (33). A stop-cock (73) may be provided to maintain the desired volume of fluid (and therefore the pressure) in the balloon once the plunger (72) has been depressed or withdrawn to inject-/withdraw the fluid (77). Also, two or more syringes (71), attached in parallel fashion, can be used if desired, particularly if a significant volume of fluid (77) is required.

FIGS. 1-7 depict a preferred embodiment for use of the introduction balloon catheter. FIG. 1 shows the introduction balloon catheter with the guidewire (37) inserted into vascular incision (25), the guidewire passing through the femoral and iliac arteries into the abdominal aorta (20). Insertion may be accomplished through known techniques, including percutaneous vascular cathterization, or use of a cutdown. In many cases, a cutdown will be preferred due to the size of the catheter and the consequent size of the required incision (25).

Figure 2:
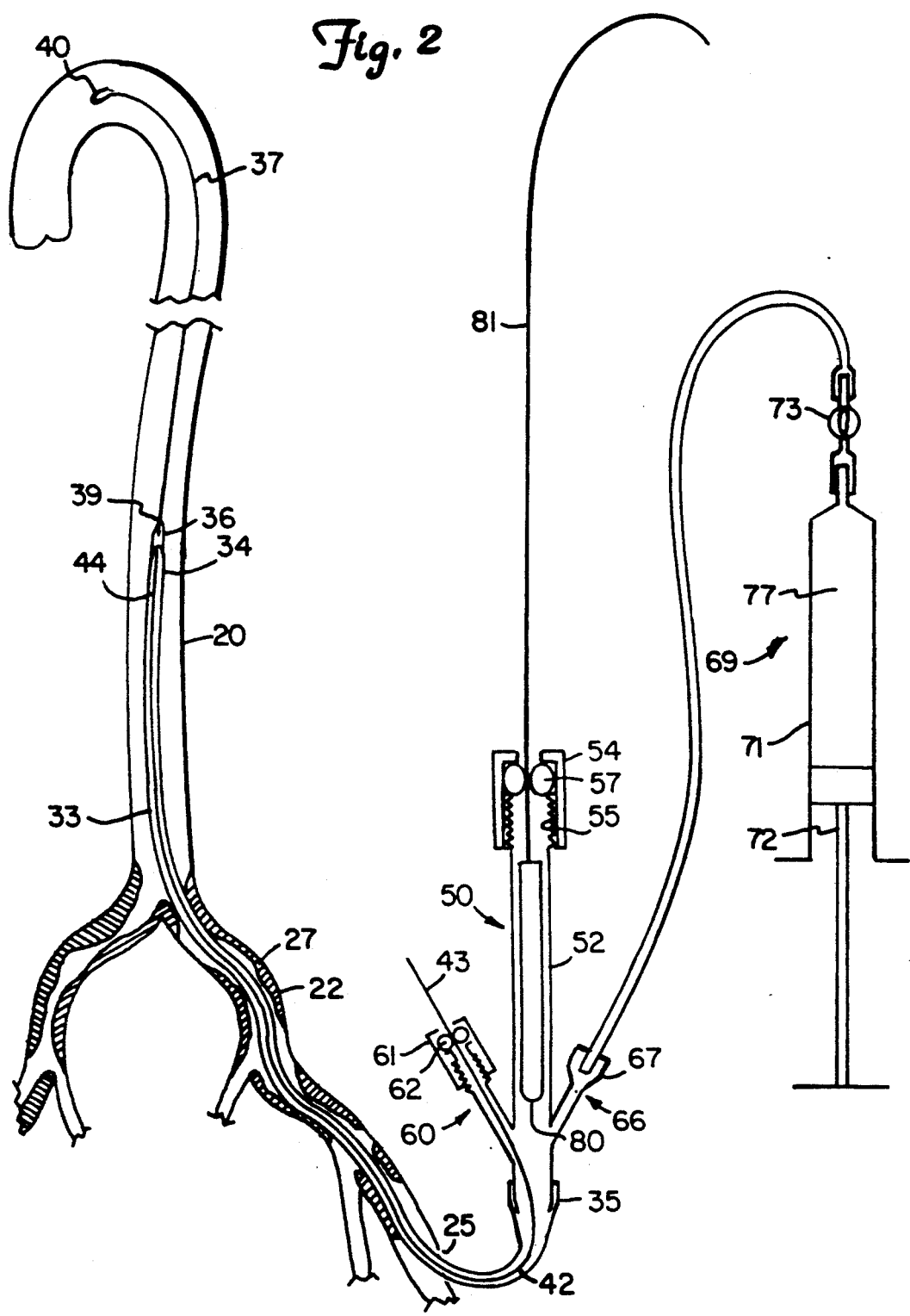
FIG. 2 shows an introduction balloon catheter of the invention with the uninflated balloon advanced into the femoral artery and partially into the abdominal aorta.

The guidewire (37) can be advanced through the femoral artery (22), past any plaque deposits (27) that may have accumulated in the artery, navigating through even a somewhat tortuous path until the distal tip (40) of the guidewire (37) reaches the much wider abdominal aorta (20). The length of the guidewire desirably is selected according to the length of the artery that must be navigated so that the tip reaches the aorta before any significant portion of the uninflated balloon (33) is inserted into the incision. If desired, however, a shorter guidewire may also be used. Upon successful advancement of the guidewire to the aorta (20), the device may be further advanced so that the uninflated balloon (33) advances into the femoral artery and partially into the aorta, as shown in FIG. 2.

In some circumstances the guidewire may not be needed. FIG. 35 shows an alternate embodiment that does not utilize a guide wire—the distal end of the balloon (shown in inflated condition) tapers to a tip that does not utilize a guidewire.

FIGS. 36-37 show yet further alternate embodiments wherein the balloon catheter includes a distal tip portion having a lumen (29); the lumen includes a side port 30 (FIG. 36) near the proximal end of the tip portion through which the guidewire (37) enters the lumen (29). FIG. 37 shows a slightly different configuration for the port (30'). In using either of these embodiments, the guidewire (37) desirably is first advanced the desired distance into the vascular passageway, and the distal tip porticn of the balloon catheter with the lumen (29) (along with the balloon) is then advanced over the guidewire. Once the balloor catheter is in proper position, the guidewire may be either left in place or withdrawn, as desired. An advantage of this configuration is that it allows the guidewire to have a conventional steerable tip, if desired, and the length that the guidewire advances into the vascular passageway can be controlled independent of advancement of the balloon into the passageway.

Once the uninflated balloon (33) has been advanced sufficiently into the abdominal aorta (20), the balloon may be inflated. The balloon should be advanced sufficiently far so that the length of the balloon in the abdominal aorta (i.e., in the wider portion of the bodily passageway) exceeds the length of the device (80) being delivered. In this way the device (80) can be advanced completely through the more narrow portion of the passageway and into the wider portion of the passageway before the device (80) is freed from the balloon.

Figure 3:
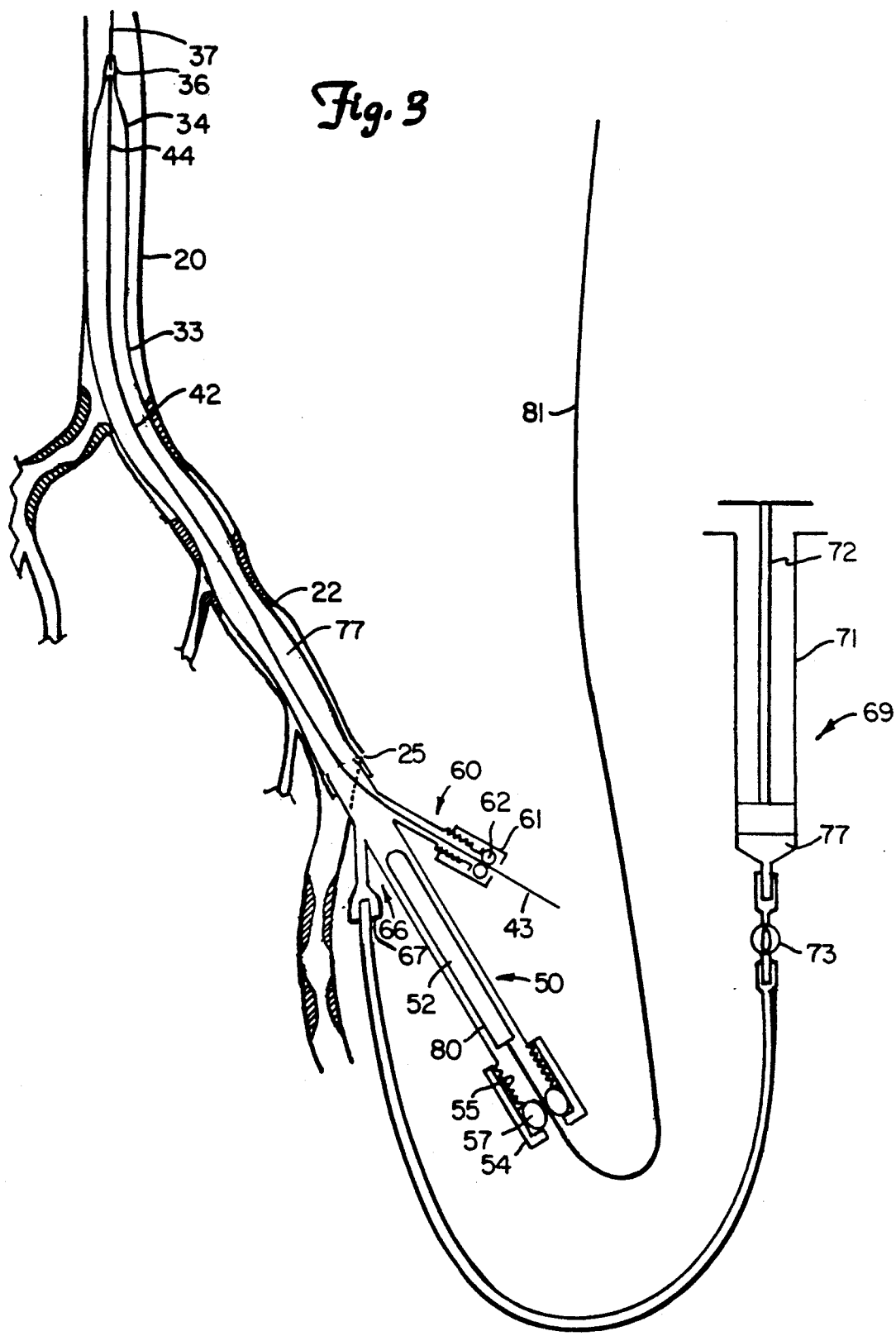
FIG. 3 shows an introduction balloon catheter of the invention inserted into the femoral artery and aorta with the balloon inflated.

Inflation of the balloon can be accomplished by conventional technigues. For example. FIG. 3 shows that the plunger (72) of the syringe (71) has been depressed to inject the fluid (77) through the fluid port (66) into the balloon (33), thereby inflating the balloon to its full diameter. Note that the inflated, stiffened balloon (33) tends to straighten the tortuosity of the passageway (in this case, the femoral artery (22)), and simultaneously performs a balloon angioplasty on any plague (27) that may be partially occluding the artery (22).

Figure 4:
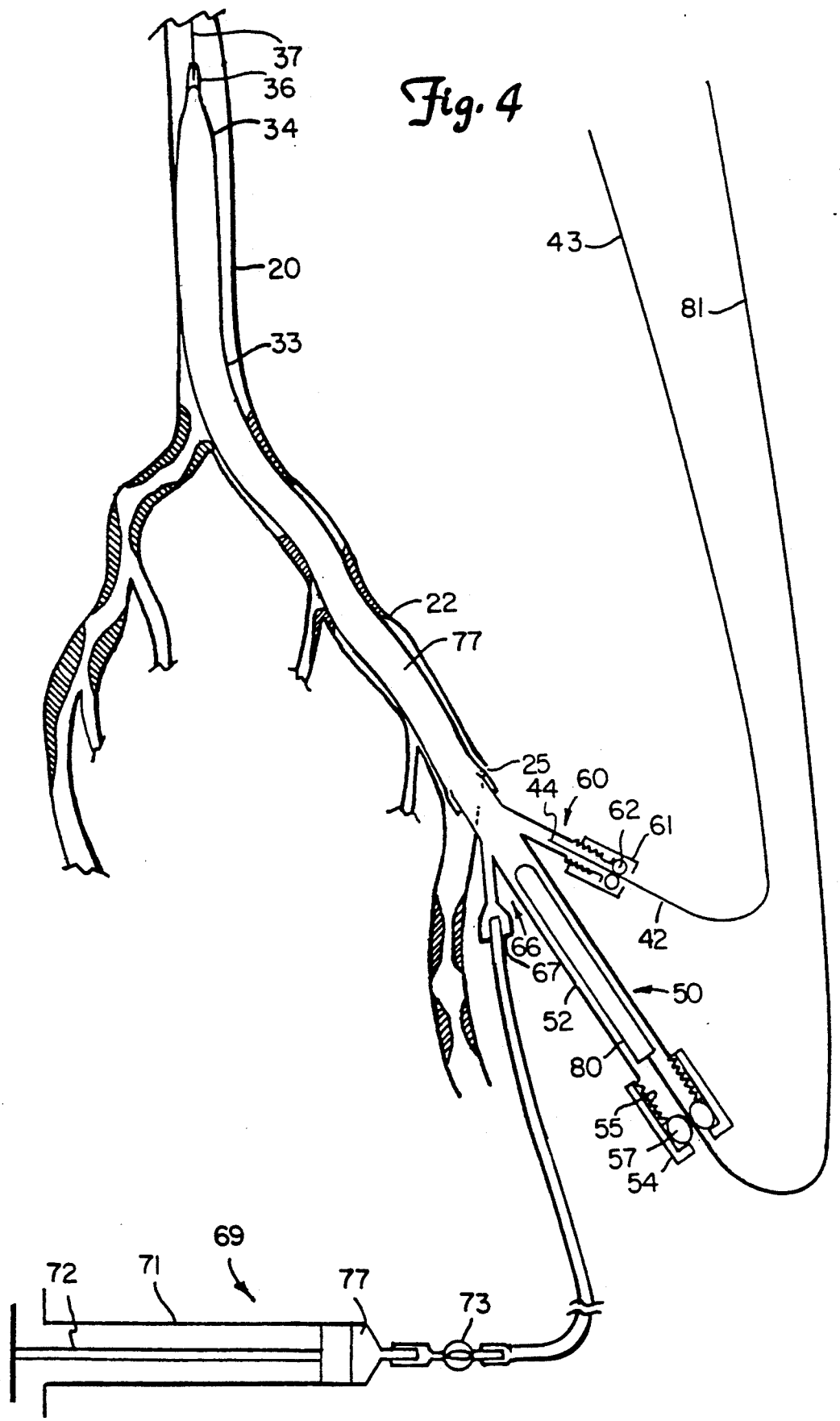
FIG. 4 shows the introduction balloon catheter of FIG. 3 with the balloon shaft retracted.

At this stage, if desired, the balloon shaft (42) may be removed, as shown in FIG. 4. Detachment of the distal end (44) of the shaft (42) from the distal fitting (36) of the balloon (33) may be accomplished by unscrewing complementary threads in the two parts, by merely pulling on the shaft against a friction fit between the tw,o parts, or by retracting it from a nonfriction site of abuttment (or by any other suitable fashion). As shown in FIG. 4, the shaft need not be completely removed from the shaft port (60), but may, if desired, be merely withdrawn sufficiently to be out of the way of advancement of the device (80) frcm the introduction chamber (50) into the balloon (33).

Figure 5:
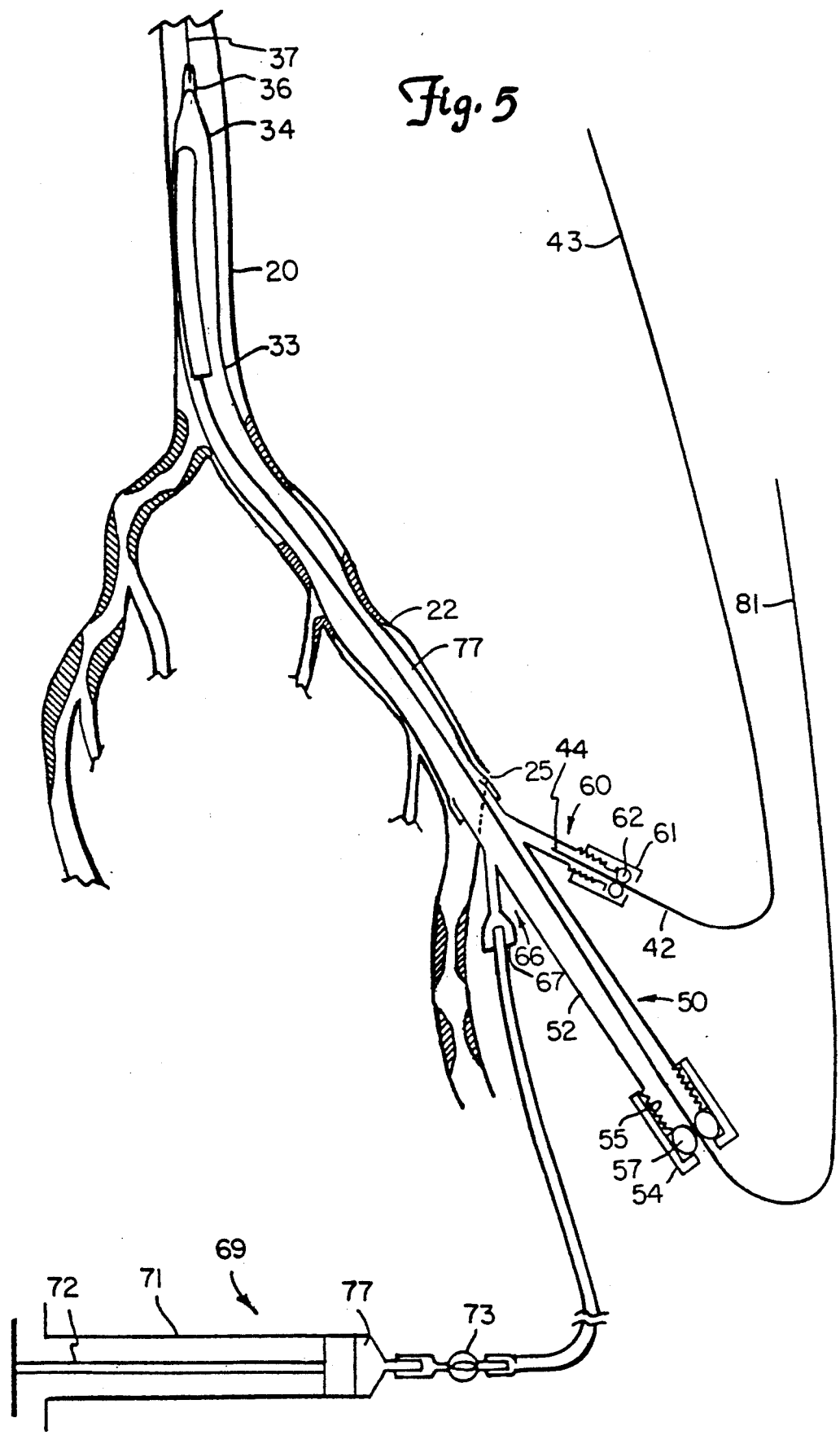
FIG. 5 shows the introduction balloon catheter of FIG. 4 with the device advanced into the distal portion of the balloon in the aorta.
Figure 6:
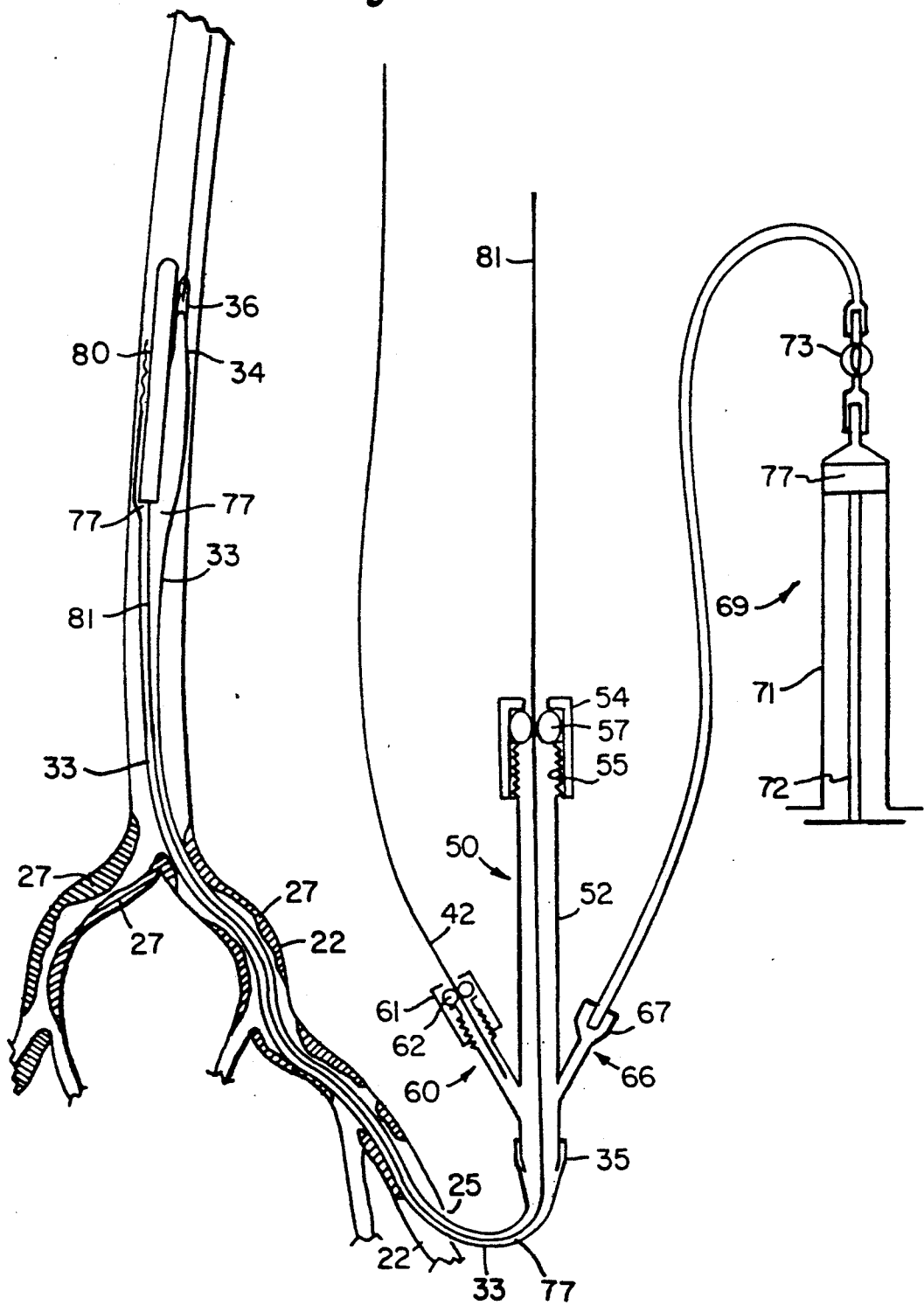
FIG. 6 shows the introduction balloon catheter of FIG. 5 with the balloon ruptured and the device partially advanced out of the balloon.
Figure 7:
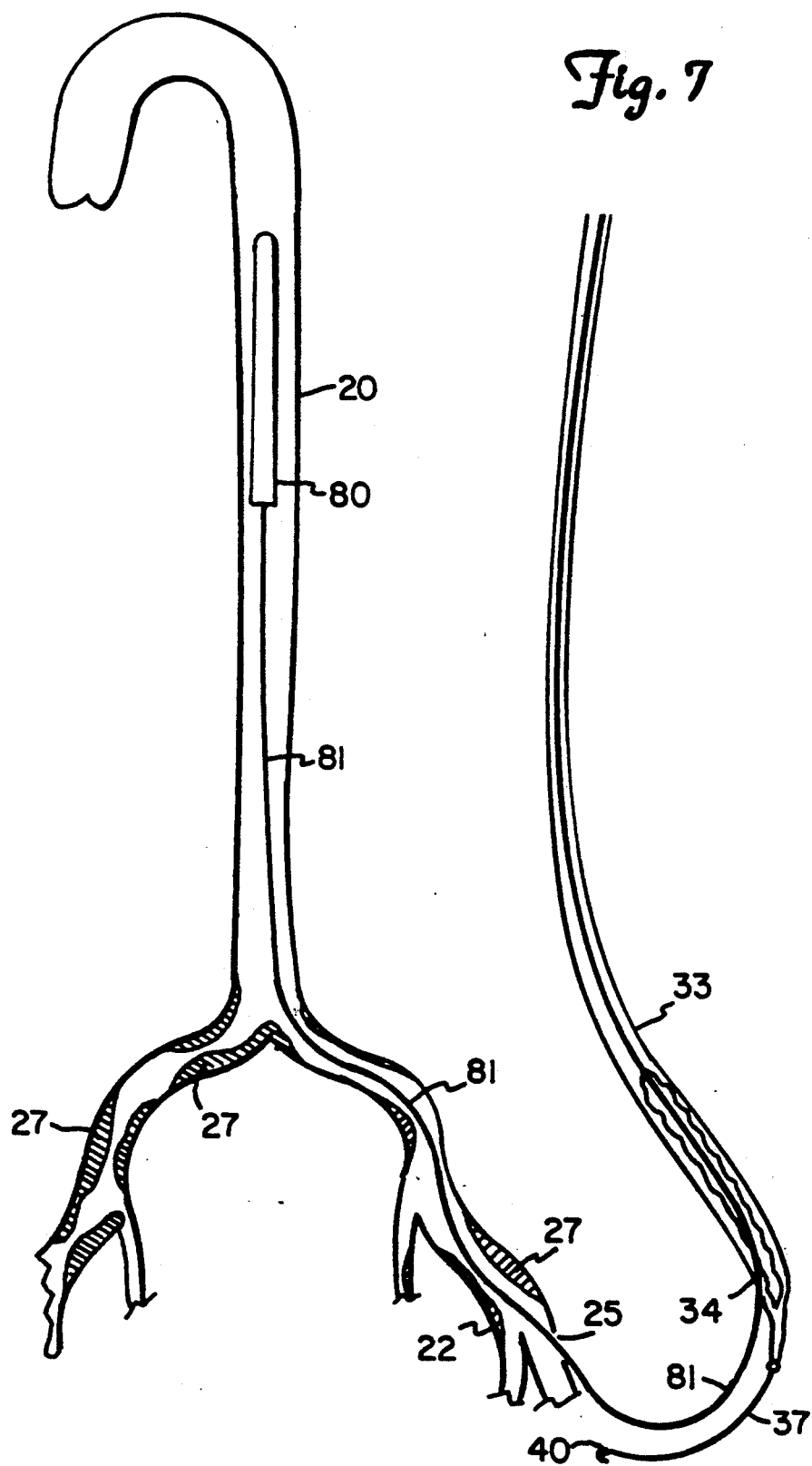
FIG. 7 shows the introduction balloon catheter of FIG. 6 with the ruptured balloon removed from the artery.

Once the balloon shaft (42) has been withdrawn (if necessary), the device (80) may be advanced through the balloon without being restricted by the otherwise tortuous and possibly plague laden artery (22) into the distal portion of the balloon (33) located in the abdominal aorta (20), as shown in FIG. 5. At this point, the balloon is ruptured near its distal end (34), freeing the device (80) to be further advanced through the aorta toward its destination, as shown in FIG. 6. The ruptured balloon may then be withdrawn from the artery (22), as shown in FIG. 7.

Figure 12:
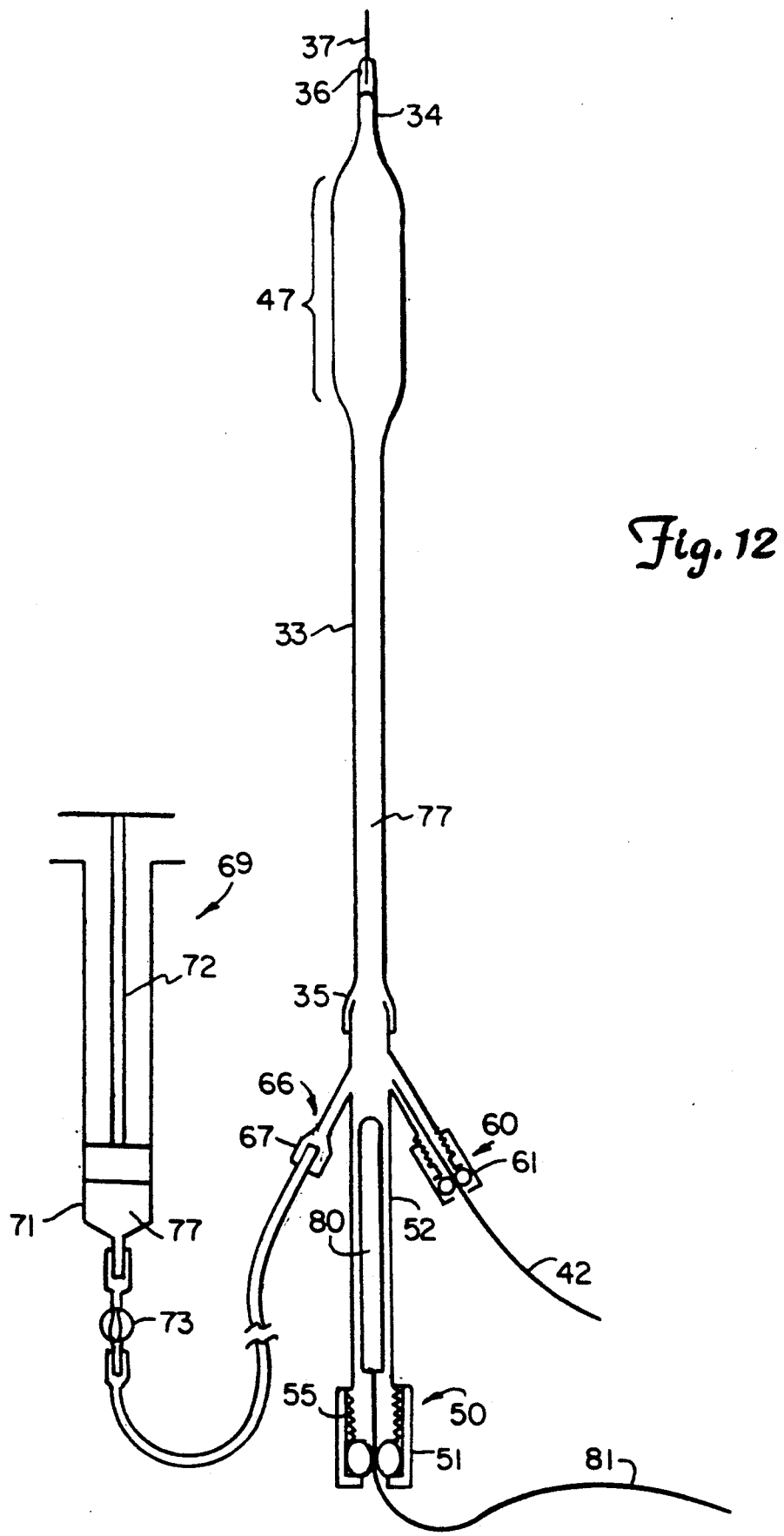
FIG. 12 shows an introduction balloon catheter of the invention having a balloon with a wider distal portion.

Rupture of the balloon may be accomplished by any suitable means or method. If the distal tip of the device (80) being advanced through the balloon includes any retractable/controllable sharp or cutting surfaces, these may be used to puncture the distal end (34) of the talloon (33). Alternately, and preferably, however, the balloon may be ruptured by increasing the pressure of the fluid (77) from the inflation device (69) until the balloon ruptures from the over-pressure. The site of the rupture in the ballocn can be controlled by manufacturing the balloon in any one of several ways. FIGS. 9-10 depict a balloon having a longitudinal segment of weakngss manufactured into the balloon which will rupture when excessive pressure is applied to the fluid (77) in the balloon. FIG. 11 shows fluid escaping from the balloon after the rupture has occurred. FIG. 12 depicts another embodiment in which the balloon has a wider (i.e. a larger diameter) distal portion (47). Upon application of excessive fluid pressure to this balloon, the excessive hoop stress (i.e., circumferential tension) in the wider portion will cause this portion to rupture before the narrower portions of the balloon rupture.

In either case, it is desirable that t:he rupture occur as a longitudinal split in the balloon, rather than a transverse split. A longitudinal split (as shown in FIG. 6) allows the device to more easily escape the balloon, and also assures that the distal portion (34) of the balloon (33) does not become separated from the proximal end (35) of the balloon.

Any other suitable means and methods may also be used to release the device (80) from the balloon. Moreover, in some circumstances, it may not even be necessary to release the device from the balloon, depending upon the task being accomplished by the device (80).

If the device delivery shaft (81) is to be temporarily left in the patient, preferably a prosthetic vascular graft (85) will have been sutured to the artery prior to introduction of the balloon and the device, as shown in FIG. 8. The graft may then be secured about the delivery shaft (81) to prevent escape of blood but permitting later removal of the device (80).

If the device (80) is of the type intended to be left in the patient only temporarily, the device can later be withdrawn using the device delivery shaft (81). In some patients the mere fact that it is easier to withdraw a device by pulling than to advance a device by pushing will be sufficient to allow removal of the device (80) by merely pulling on the shaft (81). Moreover, the fact that an angioplasty has been performed on the artery by the balloon (33) will make withdrawal easier than it otherwise would have been. In some patients, however, assistance may be needed in withdrawing the device (80) through the femoral artery (22). FIGS. 19-24 depict several embodiments of devices helpful in withdrawing the device (80).

Figure 19:
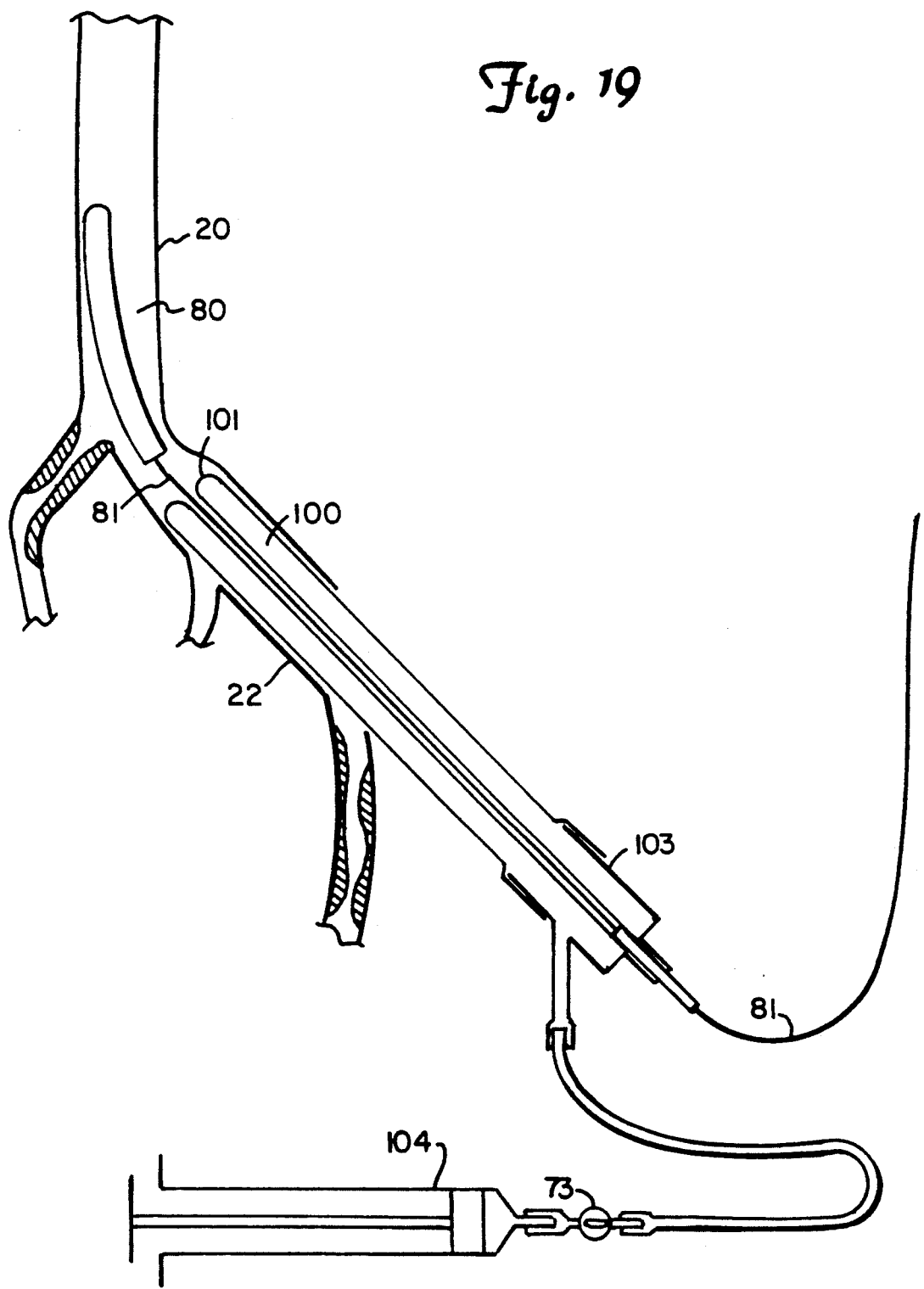
FIG. 19 shows a removal balloon catheter useful in conjunction with the introduction balloon catheter of the invention.

FIG. 19 shows a withdrawal balloon catheter (100) having an elongated configuration and a balloon with a rather blunt distal end (101). The balloon catheter includes a central lumen through which the device delivery shaft (81) is received, and a proximal Y-connector (103) to which an inflation syringe (104) is connected. In use, the device (80) is withdrawn as far as possible without the aid of the withdrawal balloon catheter (100). The balloon catheter (100) is then inserted to a position abutting the proximal end of the device (80), and the balloon is then inflated by the inflation syringe (104). This expands the portion of the artery at the proximal end of the device (80). The balloon catheter (100) is then deflated, withdrawn slightly, and reinflated to again expand the artery sufficiently (as shown in FIG. 19) to facilitate withdrawal of the device (80) a short distance until the proximal end of the device again abuts the distal end (101) of the balloon catheter (100). At this point, the balloon catheter is deflated, withdrawn a short distance, and reinflated, allowing the device (80) to be withdrawn another short distance. By repeating this procedure a few times, the device can be withdrawn the required distance, past the tortuous or narrowed portions of the artery (22) until it either has exited the incision (25) or can be freely withdrawn the rest of the way without further aid from the withdrawal balloon catheter (100).

FIGS. 20-21 show a slightly different version of the withdrawal balloon catheter, wherein the balloon (106) is relatively short but retains the blunt distal end (107). The blunt distal end of the balloon on both versions of the withdrawal balloon catheters is desirable, as it allows the proximal end of the device (80) to closely approach the full widened diameter of the balloon—if the distal end of the balloon tapers more gently, the effectiveness in expanding the artery adjacent the proximal end of the device (80) is lessened.

Figures 22, 23, 24:
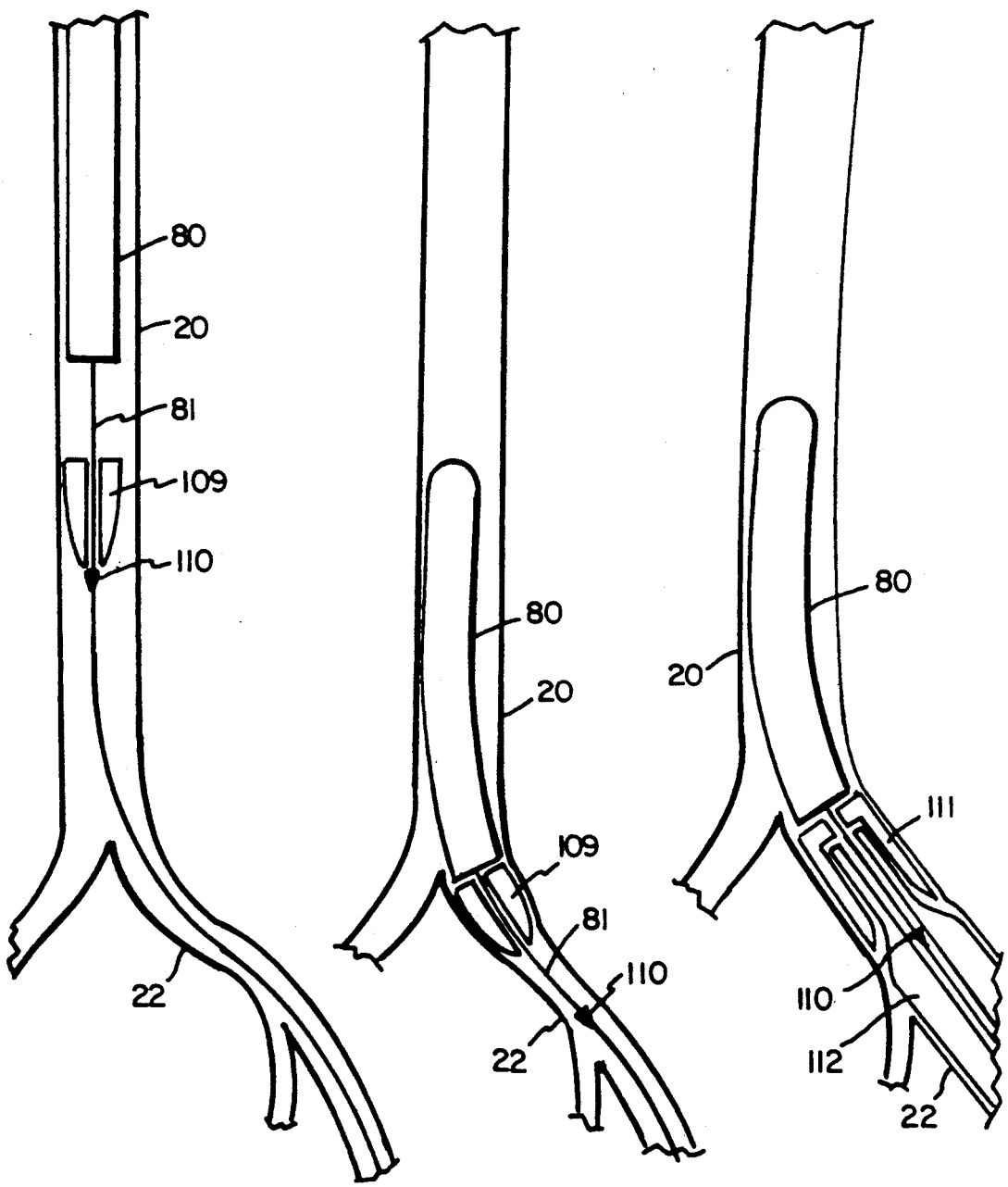
FIGS. 22-23 show consecutive steps in use of yet another apparatus useful in assisting removal of a device from a bodily passageway.
FIG. 24 shows an alternate embodiment of the apparatus of FIGS. 22-23.

FIGS. 22-24 depict yet further embodiments of withdrawal devices usable with present invention. In FIGS. 22-23, a tapered fairing (109) is carried on the device delivery shaft (81) proximal of the device (80). The outer diameter of the fairing (109) at its distal end preferably matches the outer diameter of the proximal end of the device (80). The fairing (109) then tapers to become narrower at its proximal end. A stop (110) is provided on the device delivery shaft proximal of the device (80) to advance the fairing (109) during introduction of the device and to keep the fairing (109) from drifting downstream during the time the device is in the patient. When the device is to be removed from the patient, the delivery shaft (81) is withdrawn, permitting the fairing to enter the smaller artery (22). When any resistance in the artery (22) is encountered, the fairing slides along the shaft (81) until it abuts the device (80), whereupon the two together may be pulled through the artery (22), the fairing acting to expand any narrowed portions of the artery (22).

FIG. 24 shows a slightly different embodiment, wherein the proximal end of the fairing (111) includes an inner conical section sized to receive the distal end of a conventionally tapered withdrawal balloon (112)—such balloons may be easier to manufacture than the blunt-end balloons shown in FIGS. 19, 20-21, and the fairing (111) here serves to convert the distal end of such tapered balloons into a more blunt configuration. The fairing may be manufactured from silicone, pyrolytic carbon, or any other biocompatible materials.

The balloon (33) may be manufactured from known balloon materials. Typically, such balloons are made from a biologically compatible material that is not significantly stretchable. This allows careful selection of the size of the balloon to correspond to the diameter of the artery (or other passageway) through which the device (80) is to be introduced. That is, upon inflation of the balloon, the balloon will inflate to its predetermined size, and not larger. Moreover, upon over-inflation of the balloon, the balloon will not continue to distend and further expand the artery (which, at some point would become dangerous). Rather, the balloon will rupture, typically at its weakest point which, as discussed above, desirably will be near its distal end where the balloon has been manufactured with a predisposition to rupture in a longitudinal fashion.

Figure 25:
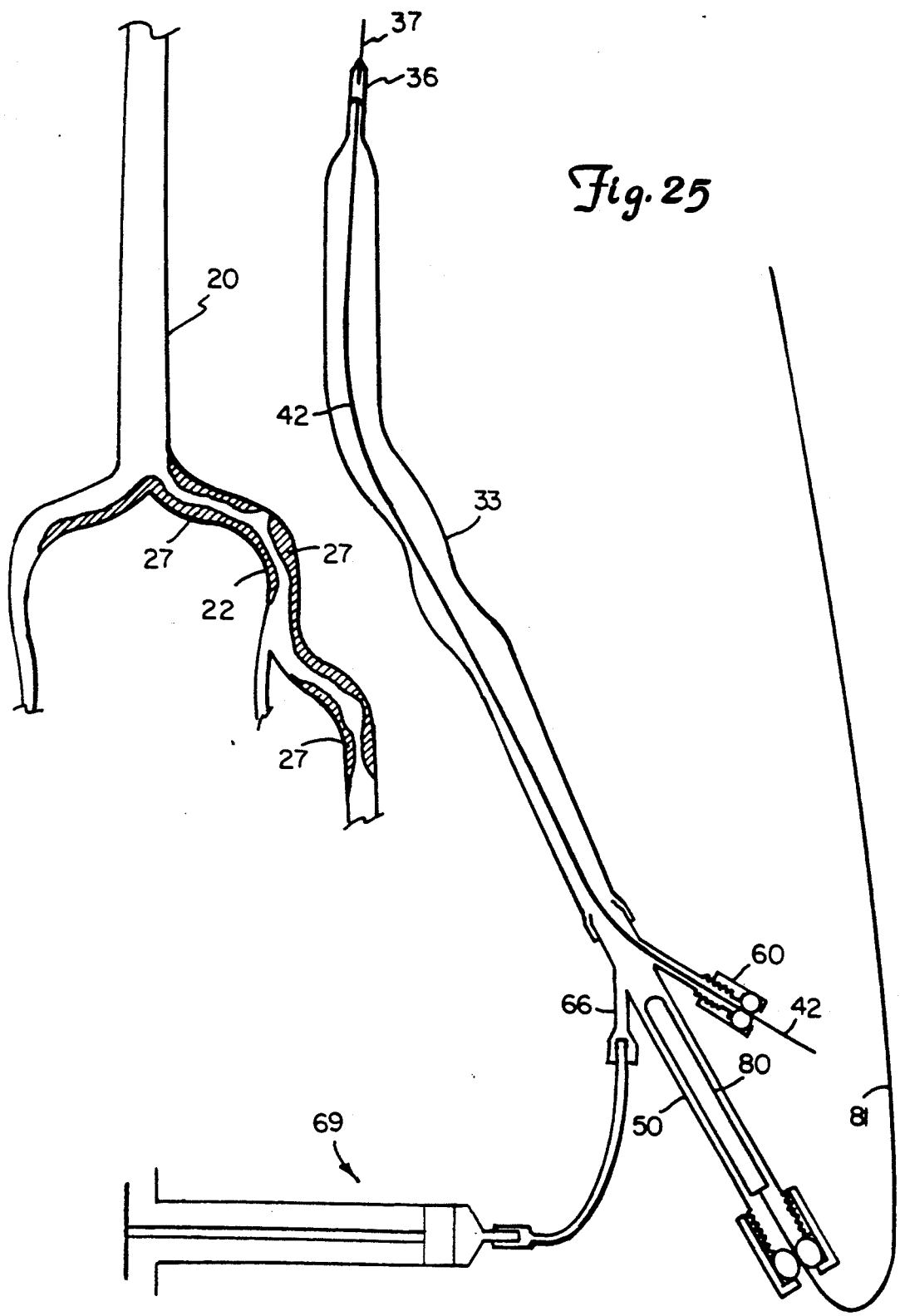
FIG. 25 shows an introduction balloon catheter of the invention that has been preformed to have certain curves when it is inflated.

Prior to inflation, the balloon may be closely furled about the balloon shaft (42) for ease of insertion and advancement of the balloon through the bodily passageway. This can be accomplished by any suitable method ordinarily used with conventional angioplasty balloons, including drawing a vacuum on the balloon with the inflation device (69), and/or during manufacture of the device by gently securing the balloon (33) in a furled configuration. If necessary, assistance for retaining the balloon in a furled configuration can be obtained by use of a biocompatible adhesive such as sugar or other similar substances. Also, to reduce excessive stress on the artery (or other passageway) due to the straightening of the balloon, the balloon may be manufactured with predetermined, slight curves, as shown in FIG. 25. Such curves should be gentle enough to permit easy advancement of the device (80).

The balloon shaft (42) serves mainly to give the balloon catheter good pushability, i.e., make the uninflated balloon catheter rigid enough so that it can be advanced into the bodily passageway. As such, the shaft (42) may be manufactured from any suitable plastic, metal, composite, or other suitable material or combinations of materials, but should be sufficiently flexible to permit it to navigate the curves of the bodily passageway. Desirably it is also radiopague. If the balloon itself can be manufactured to be stiff enough in its furled but uninflated configuration, the balloon shaft (42) could be omitted. Also, although the shaft (42) is depicted in the drawings as being located generally coaxially of the inflated balloon (33), the shaft (42) could also be attached to one wall of the balloon (33). In this configuration, it sometimes may not be necessary to remove the shaft (42) prior to advancement of the device (80) through the balloon (33). Alternately, the shaft (42) could be located outside the balloon, with the balloon externally attached to the shaft as shown in FIGS. 32–34. In this configuration the balloon shaft (42) desirably includes a central lumen through which the guidewire (37) may pass, and the balloon, (shown uninflated in FIG. 32) includes a distal loop (31) through which the guidewire (37) passes and against which the balloon shaft (42) pushes when the balloon is advanced into the artery. FIGS. 33 and 34 illustrate that the guidewire (37) may be withdrawn into the shaft (42) after the balloon has been advanced to the proper location, and then the two devices can be simultaneously withdrawn (preferably after the balloon has been at least partially inflated), leaving the balloon in place.

Selection of the appropriate balloon configuration for a particular procedure may depend upo the configuration of the device (80), including whether the presence of the balloon shaft (42) (whether or not it is attached to the balloon wall) significantly reduces the effective diameter of the balloon and therefore the maximum size of the device (80) that can be introduced through the balloon.

Figure 15:
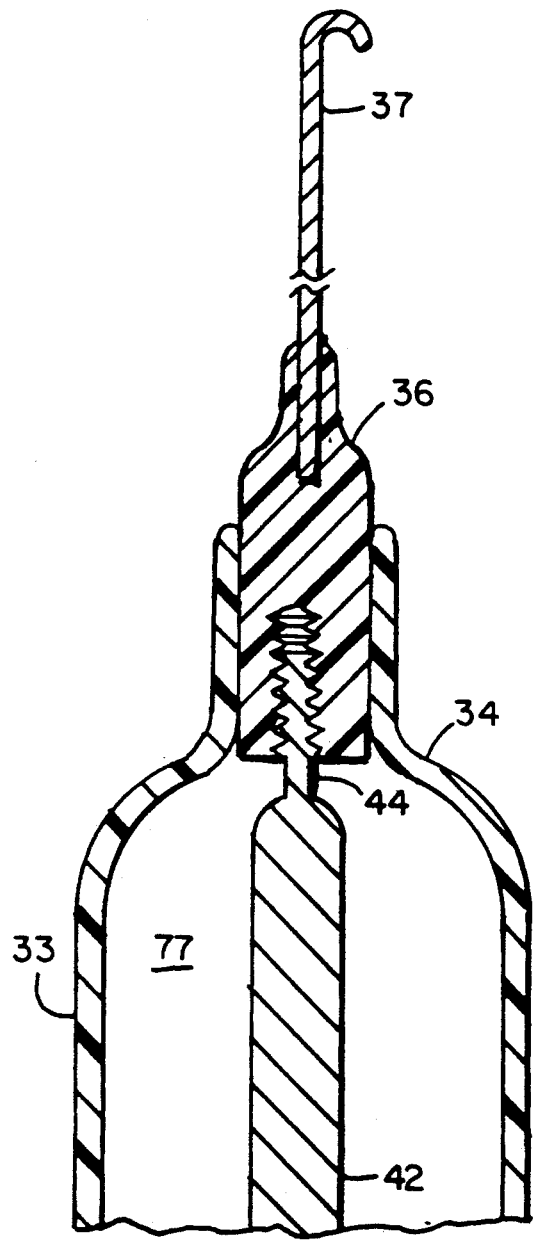
FIG. 15 is a broken-away, crrss-sectional view of the distal end of the balloon catheter of the invention.
Figure 16:
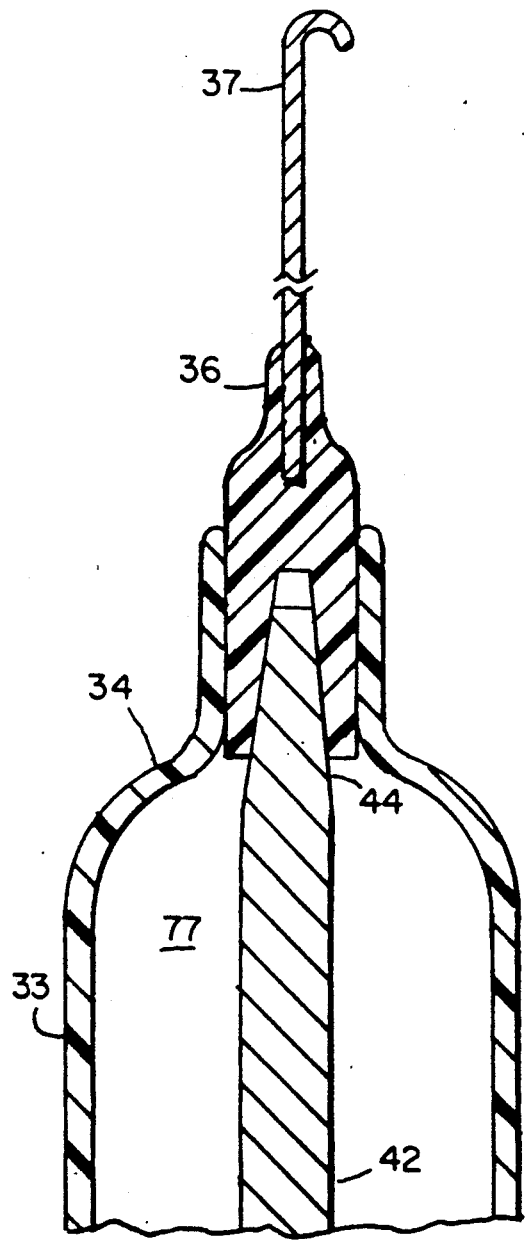
FIG. 16 is a broken-away, cross-sectional view similar to FIG. 15 of an alternate embodiment of the invention.
Figure 17:
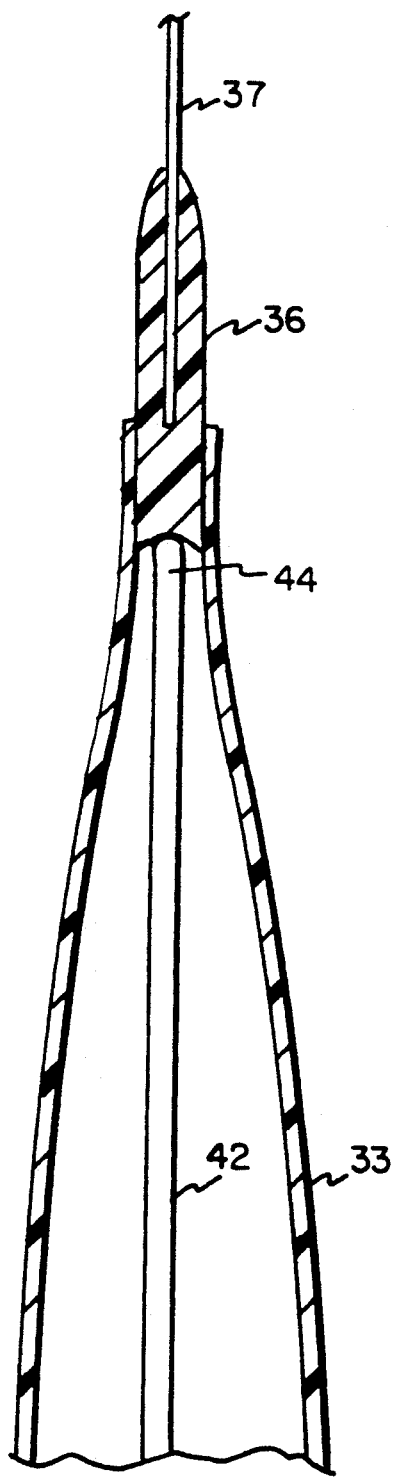
FIGS. 17-18 show yet another cross-sectional view similar to FIG. 16 of an alternate embodiment of the invention.
Figure 18:
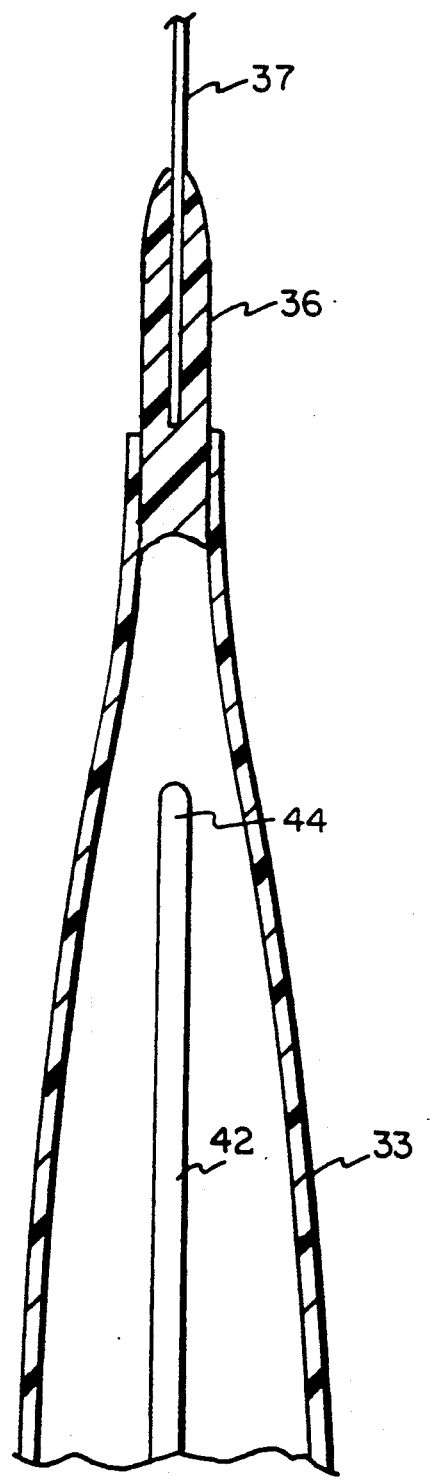

If a detachable balloon shaft (42) is utilized, the distal end (42) of the balloon shaft includes engagement means for engaging and disengaging the shaft (42) to and from the distal end of the balloon. This engagement means may comprise any suitable mechanism. Complementary threads may be formed on the distal end (44) of the shaft (42) and on the balloon distal fitting (36), as shown in FIG. 15. Alternately, a friction fit may simply be utilized between these two parts, as shown in FIG. 16. In yet another embodiment, shown in FIGS. 17–18, the distal end (44) merely abuts the balloon distal fitting (36), the shaft's distal end (44) being loosely received in the distal portion of the balloon which tapers to a narrow end—as the balloon shaft (42) is advanced, it pushes against the fitting (36), but the shaft (42) can be easily withdrawn without having to physically uncouple it from the balloon. If desired, a complementary cup-shaped portion can be formed in the fitting (36), but such is not necessary. Other eguivalent mechanisms may also be utilized. In any event, the engagement means should be such that the shaft (42) can be disengaged for removal without placing undue stress on the balloon (33).

The introduction chamber (50) may simply be the proximal end of the balloon (33). In most cases, however, it is desirable that the chamber (50) be manufactured from a suitable rigid material. Preferably, the chamber (50) is made of a transparent but rigid plastic material permitting visual inspection of the device housed in tile main chamber (52) as well as the presence or absence of fluid, air, or other substances. Assemblies such as the introduction chamber (50) are well known, freguently referred to as "Y-connectors." Similarly, the compression fittings (54) and (61) on the introduction chamber (50) are also well known. Though not shown in the drawings, the introduction chamber (50) may also include means for permitting withdrawal of air from the chamber, either through a bleedable port, or by inserting a hypodermic needle through a rubber seal, or any other suitable means. Air may also be bled from the chamber (50) by loosening the fitting (54). By orienting the entire device and the patient so that any air in it rises into the introduction chamber (50) the air can be bled off, preventing it from being released into the patient when the balloon is ruptured.

Figure 26:
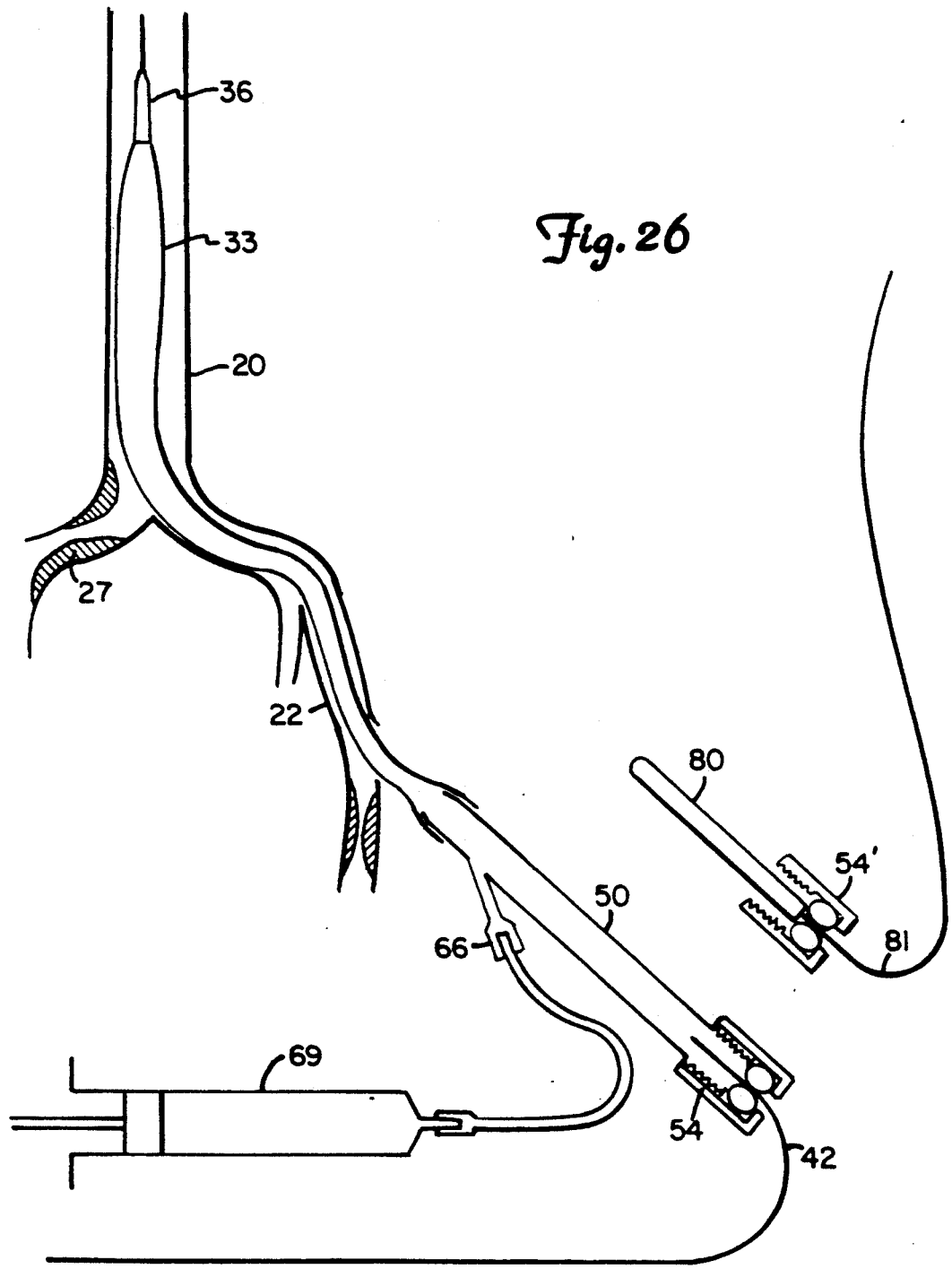
FIG. 26 shows a simplified version of the introduction balloon catheter of the invention.

The various drawings show a variety of combinations of possibilities for the location, configuration, and number of ports associated with the introduction chamber (50). FIG. 26 shows a simplified version in which only a single fluid port (66) is utilized. As shown in this drawing, once the uninflated balloon is advanced into the artery and aorta (20), the balloon shaft (42) may be withdrawn and the introduction chamber fitting (54) removed and replaced with a fitting (54') assembled to the device (80), whereupon the balloon may be inflated. Alternately, the same fitting (54) may be utilized if the fitting (54) can be advanced over the proximal end of the delivery shaft (81) (sometimes this may be inhibited by other apparatus that has been attached to the shaft's (81) proximal end, reguiring pre-assembly of a fitting (54') on the shaft), and if the outer diameters of the balloon shaft (42) and the device delivery shaft (81) are close in diameter.

The inflation device may comprise any suitable inflation device such as those typically used in balloon angioplasty. Typically, the inflation device (69) will include a syringe (71) having a plunger (72) for expelling the fluid (77) into the balloon (33). If needed to increase the capacity of the inflation device, a plurality of syringes may be used in parallel, permitting one to be replenished with fluid when the other is in use. A stop-cock (73) may be provided to maintain pressure on the system. A pressure gauge (not shown) may also be utilized to precisely monitor the amount of pressure in the balloon (33). A good synopsis of these traditional angioplasty supplies appears in T. Ischinger, *Practice of Coronary Angioplasty*, Chapter 7 (1986).

The inflation fluid (77) should be a biocompatible fluid, such as saline, since some of the fluid will enter the passageway when the balloon is ruptured. When the invention is used to introduce a device to the vascular system, either a saline/anticoagulant (such as heparin) mixture and/or radiographic contrast solutions and/or other biocompatible fluids may be utilized. In most such applications, the volume of fluid (77) actually introduced into the body is small enough that such solutions will suffice. Moreover, if, in certain applications, repeated introductions are made and the volume of fluid (77) becomes significant, plasr1a or whole blood could be utilized as the fluid, though this normally would not be necessary.

Alternately, if desired, some of the fluid can be withdrawn from the balloon before the balloon is ruptured. Rupture can be accomplished by means other than over-pressure, such as by puncturing the balloon with the distal end of the device, or the like. In an alternate embodiment shown in FIGS. 27–30, withdrawal of fluid and rupture by overpressure can both be accomplished. In this embodiment, an isolating balloon (90) is provided within the introduction balloon (33) proximally cf the device (80), but preferably coaxially of the device delivery shaft (81). After the device (80) has been advanced into the aorta (20), the isolating balloon (90) can be advanced to a position just proximal of the device (80). When so positioned, the isolating balloon (90) can be inflated, as shown in FIG. 28 by injecting fluid from the inflation syringe (96) through the inflation lumen (92). Fluid (77) can then be withdrawn from the proximal portion of the introduction balloon (33) into inflation device (69) without releasing pressure in the distal end portion of the balloon (33) (see FIG. 29). The distal end portion of the balloon (33) can then be ruptured by overpressure supplied by an additional syringe (98) injecting fluid through a second lumen (93) in the isolation balloon shaft that delivers the fluid distally of the isolation balloon (90).

Figure 27:
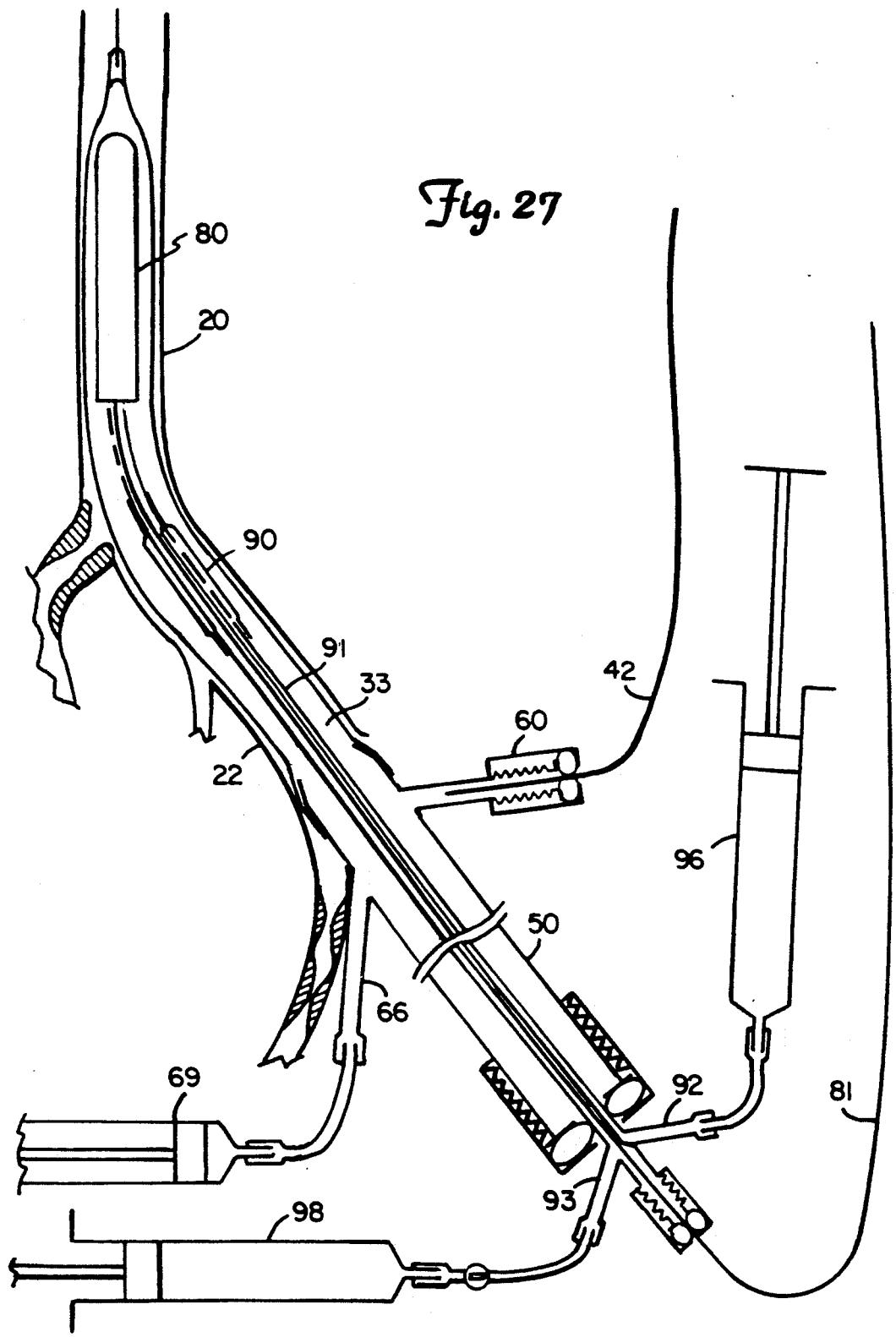
FIGS. 27-29 show a configuration and method for reducing the volume of fluid released into the vessel when the balloon catheter is ruptured.
Figure 28:
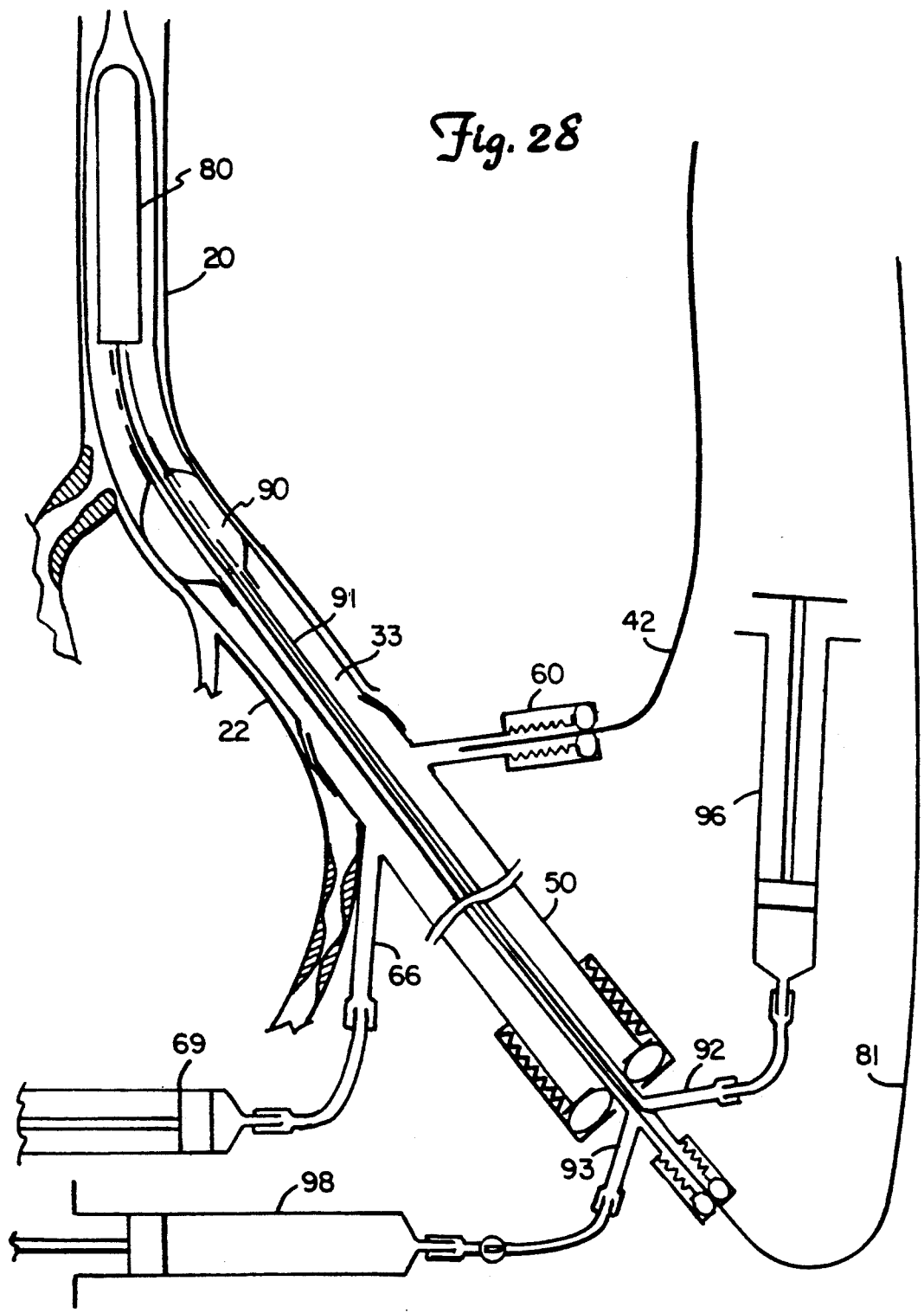
Figure 29:
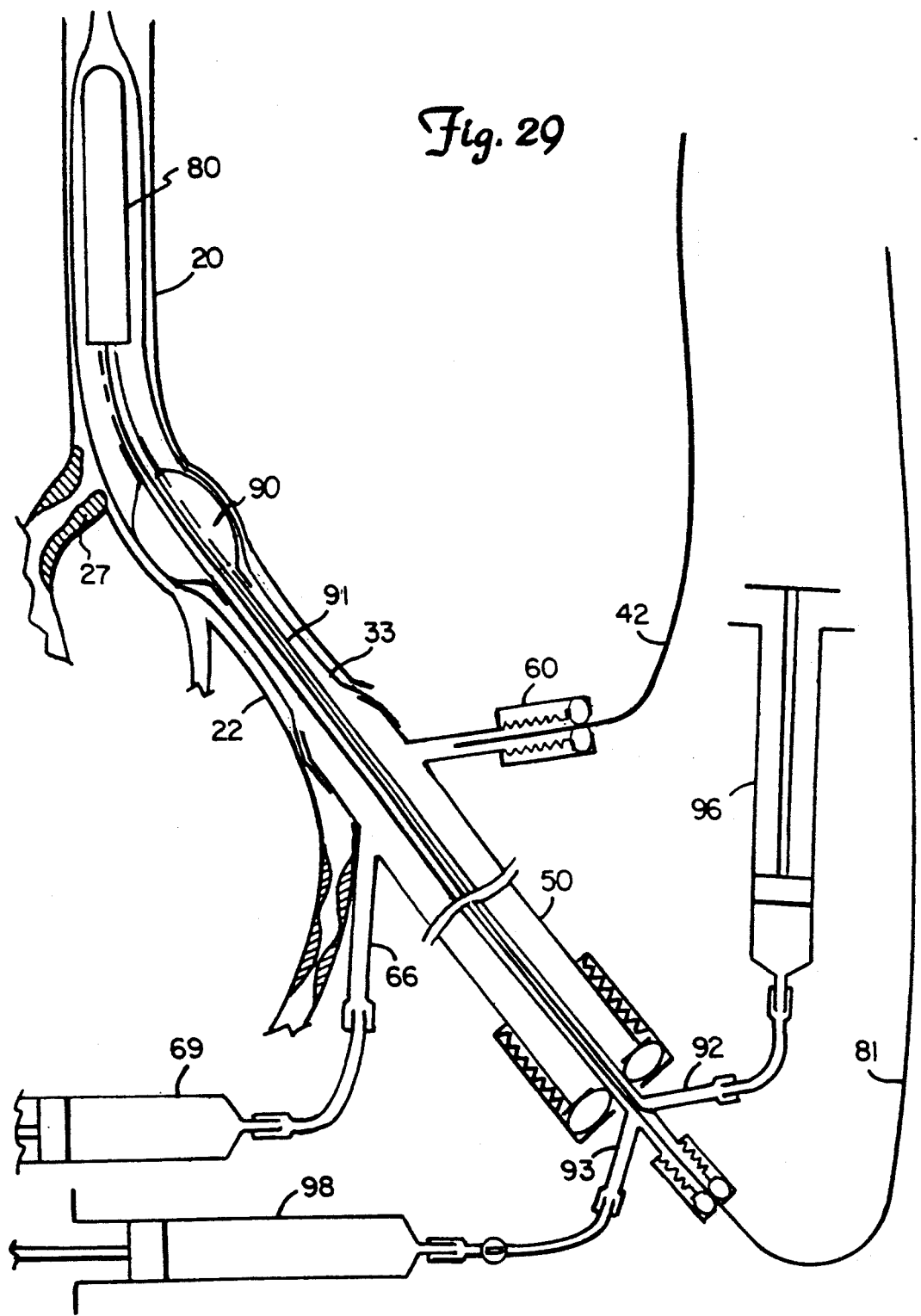

FIG. 30 shows yet a further embodiment, similar to the embodiment of FIGS. 27-29, but slightly simpler. In this embodiment, the inflation device (69) is connected directly to the central lumen (93) of the isolating balloon (90), eliminating the need for the separat( syringe (98) of FIGS. 27-29. The inflation device serves initially to inflate the entire introduction balloon (33) to permit advancement of the device (80) into the distal portion of the balloon (33). Prior to inflation of the isolation balloon however, the entire introduction balloon (33) is deflated by withdrawing fluid into the inflation device (69). Then the isolation balloon (90) may be inflated, causing the inflation device (69) to be in connection only with the distal end portion of the balloon (33); overpressure supplied by the inflation device (69) will then rupture the distal portion of the balloon (33), freeing the device (80) from the balloon.

The device (80) to be delivered through the introduction balloon catheter of the invention may be of virtually any type, and it is contemplated that a wide variety of devices could be utilized. One of the possible uses is the delivery of devices to the heart through the femoral artery. By way of illustration, temporary cardiac assist pumps have been proposed for use in patients having cardiogenic shock following acute myocardial infarction, or in patients who have failed to wean from cardiopulmonary bypass. Insertion of such a pump through the femoral artery has in a significant percentage of cases been difficult or impossible due to vascular disease that has impeded or blocked advancement of the pump beyond the aortoiliac junction. See, e.g., P. Rutan, et. al, *Initial Experience with the HEMOPUMP*, Critical Care Nursing Clinics of North America (Vol. 1, No. 3, September 1989); O. Frazier, et. al, *First Human Use of the Hemopump, a Catheter-Mounted Ventricular Assist Device*, Ann. Thorac. Surg. 1990; 49:299-304. This pump consists of an elongated cylindrical tube in which a propeller/impeller rotates to propel blood therethrough. The pump typically would be positioned in the descending aortic arch, passing through the aortic valve into the left ventricle, thereby pumping oxygenated blood from the left ventricle into the aorta.

The pump preferably is delivered to the aorta and heart by introduction through the femoral artery. An obvious limitation of the capacity of the pump is its diameter, and this in turn is limited by the size of the femoral artery. Heretofore, the proposed solution to delivery of the pump through disease-restricted arteries is to decrease the diameter of the pump. Utilizing the introduction balloon catheter of the invention facilitates introduction of the pump into the arteries and also alleviates the need to decrease the diameter of such a pump (and might even allow a slight increase in such diameter). Since the theoretical capacity of the pump is related to the cross-sectional size of the pump, which in turn is proportionate to the square of the radius of such cross-section, even a small change in the diameter of the pump has a significant effect on the theoretical capacity of the pump.

The device (80) depicted in the drawings is shown somewhat schematically to represent any type of device that might be delivered into a passageway, and is not intended to depict any particular device (though its relative size and configuration is not unlike the aforementioned pump). In determining the size of device (80) that may be delivered through a given balloon size, however, consideration must be given to the ability of fluid (77) to either flow around or through the device (80) as the device (80) is advanced through the inflated balloon (33) to avoid excessive pressure build-up distally of the device (80), and therefore to avoid premature rupture of the balloon (33).

Figure 13:
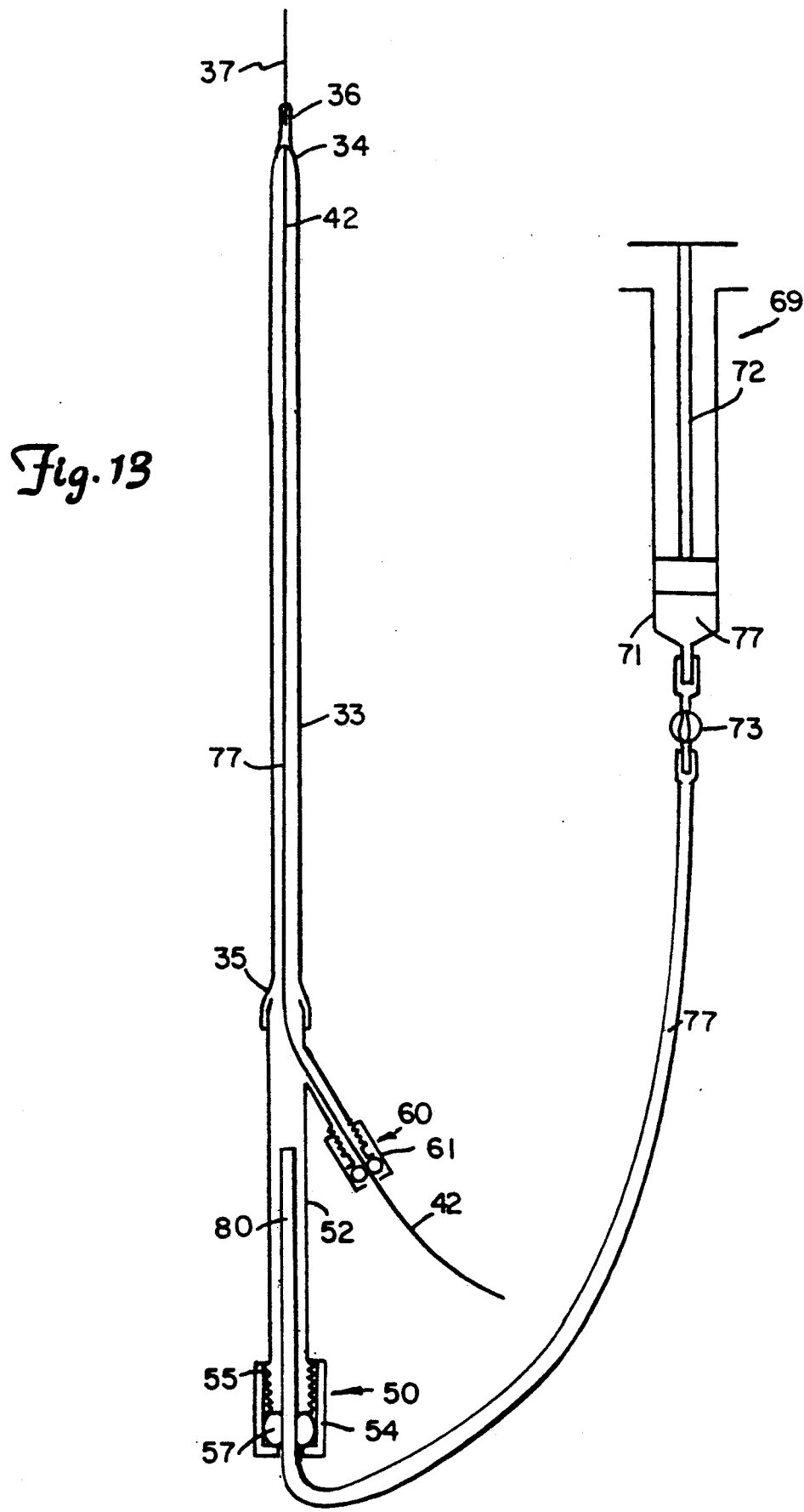
FIG. 13 shows an introduction balloon catheter of the invention where the device being inserted into the bodily passageway includes a catheter through which inflation fluid is delivered to the balloon.

FIG. 13 shows an alternative embodiment of the introduction balloon catheter of the invention. In this embodiment, the device (80) itself (a large bore catheter, for example) includes a central lumen through which the inflation fluid (77) is injected into the balloon (33), thereby alleviating the need for a separate fluid port (66). Alternately, the device delivery shaft (81) could include a lumen with a port adjacent the proximal end of the device itself (not shown). FIGS. 14 and 14A show yet another embodiment wherein the balloon shaft (42) includes a central lumen through which the fluid (77) is injected into the balloon (33). In a preferred configuration of this embodiment, shown in enlarged detail in FIG. 14A, the central lumen has an outlet port or ports near its distal end (44) so that fluid may be injected even when the shaft is almost completely withdrawn through the shaft port (60).

FIG. 31 shows yet a further embodiment where the device delivery shaft (81) is supported by a stiffening shaft (82) to aid in advancing the device (80) through the passageway—in many cases this shaft (82) need only be long enough to help push the device (80) through the balloon (33) into the aorta (20), following which the delivery shaft (81) may be advanced alone to deliver the device to its destination. A fitting (83) may be provided to seal the stiffening shaft (82) about the delivery shaft (81).

Figure 39:
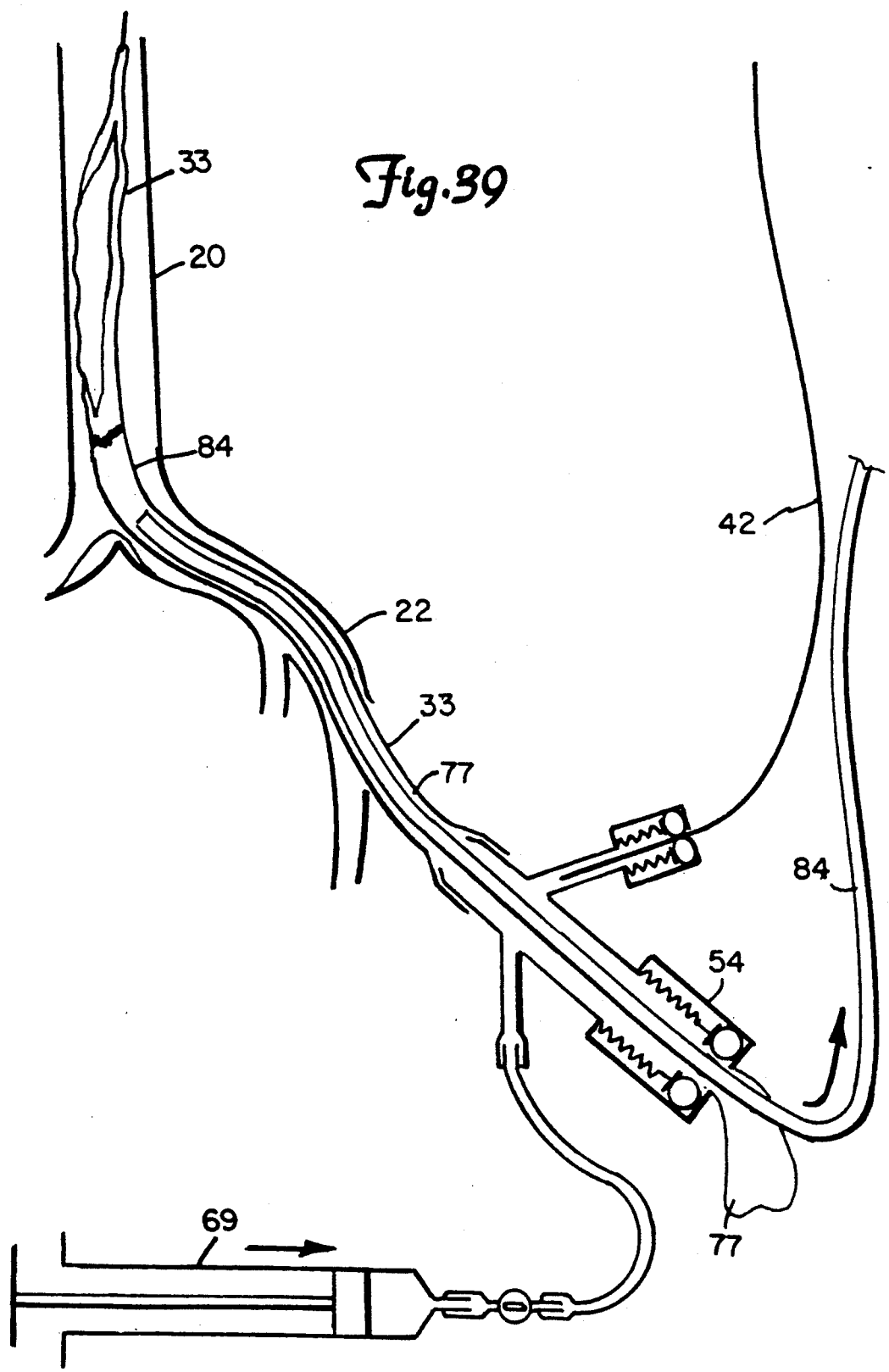

FIGS. 38-39 show yet a further embodiment in which the device to be delivered through the balloon catheter is a large bore catheter, such as the type used in a cardiopulmonary bypass support system. Such systems typically provide cardiopulmonary bypass through the femoral vein and artery to oxygenate and pump blood during cardiac arrest, acute heart failure, or similar emergency situations. Full discussion of these procedures can be found in, e.g., F. Shawl, "Emergency Cardiopulmonary Bypass Support in Patients With Cardiac Arrest in the Catheterization Laboratory," Catheterization and Cardiovascular Diagnosis 19:8-12 (1990).

In such procedures, a catheter or cannula typically is inserted into the femoral artery and the femoral vein to establish circulation through the external oxygenator/blood pump. Though venous access is not usually problematical, if a patient is atherosclerotic, arterial access may be difficult or impossible. Referring to FIG. 38, the balloon catheter (33) of the invention has been ruptured after its insertion, inflation, and advancement of the arterial access cannula (84) of a cardiopulmonary bypass support system. In this drawing, blood, which has been withdrawn from a seperate venous access cannula (not shown) has been oxygenated and is being pumped back into the aorta (20) through the arterial access cannula (84). The distal end of the cannula (84) can be advanced as far as desired in the femoral/iliac artery and the aorta (20), or need not be advanced out of the end of the ruptured balloon, as desired. As will be described below, removal of the ruptured balloon is not necessary until the cannula (84) itself is removed, and, in fact, the ruptured balloon can be used to help withdraw the cannula (84). When the balloon catheter is left in place for this purpose, desirably the fluid (77) in the inflation device (69) is a saline/anticoagulant (such as heparin) mixture which can be injected in small amounts from time to time to prevent coagulation in and about the ruptured balloon.

Because the cannula (84) is of relatively large bore and may be left in the patient for some period of time, withdrawal or repositioning of the cannula (84) sometimes is difficult due to friction between the cannula (84) and the wall of the femoral artery (22), particularly if it is atherosclerotic. FIG. 39 illustrates the utility of the balloon catheter (33) of the invention in assisting repositioning or removal of the cannula (84). In this drawing, fluid (77) is being forcefully pumped into the ruptured balloon (33) by the inflation device (69). Although the distal rupture of the balloon allows some of the fluid (77) to escape into the vascular system, a forceful injection of fluid (77) will cause at least the proximal and intermediate portions of the balloon to inflate somewhat—at least enough to allow the fluid (77) to travel distally toward the rupture. Even though the balloon may not entirely inflate, the presence and passage of the fluid through the balloon will lubricate the interface between the balloon (33) and the outer surface of the cannula (84) sufficiently to allow the cannula (84) to be repositioned or withdrawn without damage to or friction with the wall of the artery (22). If desired, the compression fitting (54) may be loosened slightly to permit easier advancement or withdrawal of the cannula (84), as shown in FIG. 39. Once the cannula (84) has been withdrawn, the balloon can easily be deflated and withdrawn.

In use, the bodily passageway through which a device (80) is to be inserted is selected, and determination of the diameter and length of that passageway is made through conventional radiology technigues, such as angiography and the like. An appropriate size introduction balloon catheter, both in diameter and length, is then selected. Appropriate anesthesia may be administered to the patient, if necessary, and entry to the passageway is obtaired. In the case of entry to the vascular system, a vascular graft may be sutured to the artery or vein after performing a cutdown procedure, or, in certain circumstances, access to the vessel may be obtained through a percutaneous puncture, as by using the Seldinger technigue (though normally a cutdown procedure will be used due to the size of the balloon selected).

The guidewire (37) is then advanced into the passageway. followed by introduction of the deflated balloon (33). When the distal portion of the balloon (33) has reached its destination (typically an enlarged area of the passageway such as the aorta), the balloon is inflated by operation of the inflation device (69), which injects fluid (77) into the balloon (33). The balloon shaft (42) may then be removed (or merely retracted). if desired. The device (80) may then be advanced into the balloon by advancing the device delivery shaft (81) through the ring (57) of the introduction chamber's (50) threaded compression fitting (54). This fitting may be loosened slightly to facilitate advancement of the delivery shaft (81), and then tightened again to reduce leakage once the device (80) has reached its destination in the balloon (33).

Upon confirmation that the device (80) is properly situated in the balloon (34), the balloon may be ruptured to free the device (80) from the balloon (33). As described above, such rupture typically may be accomplished by providing over-pressure to the balloon to burst it in a longitudinal fashion near its distal end (34). The device (80) may then be further advanced into the passageway, and the balloon (33) may be withdrawn from the passageway.

In the case of introduction of a device to the vascular system, as depicted in the drawings, inflation of the balloon will have temporarily straightened the otherwise tortuous vessel to permit easier passage of the device (80), and the balloon will also have compressed any plague (27) deposits, thus facilitating later removal of the device, if desired.

While a preferred embodiment of the present invention has been described, it shculd be understood that various changes, adaptations and modifications may be made therein without departing from the spirit of the invention and the scope of the appended claims.

What is claimed is:

1. A balloon catheter for introducing a device into a bodily passageway, the device having a predetermined maximum cross-sectional diameter, comprising:

an elongated inflatable balloon having proximal and distal ends, the balloon having a cross-sectional diameter, when deflated, smaller than the maximum cross-sectional diameter of the device being introduced into the passageway, the balloon being inflatable to define an inflated balloon cavity having a cross-sectional diameter along substantially its entire length larger than the maximum cross-sectional diameter of such device;

a removable balloon shaft;

an introduction chamber attached to the proximal end of the balloon for temporarily housing the device being introduced into the passageway, such chamber being in direct communication with the balloon cavity so that, when the balloon is inflated, the device being introduced into the passageway can be advanced from the chamber into the inflated balloon cavity; and inflation means for inflating the balloon once the balloon has been inserted into the bodily passageway, allowing advancement of the device from the introduction chamber into the inflated balloon cavity and through the balloon into the bodily passageway.

2. The balloon catheter of claim 1 further including a guidewire extending distally from the balloon.

3. The balloon catheter of claim 2 wherein the guidewire and the balloon each have proximal and distal ends, the proximal end of the guidewire being attached to the distal end of the balloon.

4. A balloon catheter for introducing a device into a bodily passageway, comprising:

an inflatable balloon;

a guidewire extending distally from the balloon;

a distal tip portion extending distally of the balloon, such tip portion including a lumen through which the guidewire may pass;

a removable balloon shaft;

an introduction chamber attached to the balloon for temporarily housing the device being introduced into the passageway; and inflation means for inflating the balloon once the balloon has been inserted into the bodily passageway, allowing advancement of the device from the introduction chamber through the balloon into the bodily passageway.

5. The balloon catheter of claim 4 wherein the lumen of the distal tip poron includes a port near the proximal end of such tip portion.

6. The balloon catheter of claim 1 wherein the balloon and the introduction chamber each having proximal and distal ends, the proximal end of the balloon being attached to the distal end of the introduction chamber.

7. The balloon catheter of claim 1 wherein the device includes a device delivery shaft at least partially disposed in the introduction chamber, and the introduction chamber includes a delivery shaft port through which at least a portion of the delivery shaft may be advanced.

8. The balloon catheter of claim 1 wherein the balloon and the balloon shaft include proximal and distal ends, respectively, the distal end of the balloon shaft being removably engagable with the distal end of the balloon.

9. The balloon catheter of claim 8 further including a shaft port in the balloon or the introduction chamber through which the balloon shaft may be at least partially withdrawn.

10. The balloon catheter of claim 9 wherein the shaft port is substantially sealable about the shaft.

11. The balloon catheter of claim 1 wherein the inflation means comprises a fluid reservoir in fluid communication with the balloon, and means for exerting pressure on the fluid to inject it into the balloon.

12. The balloon catheter of claim 11 wherein the fluid reservoir comprises a syringe.

13. The balloon catheter of claim 1 wherein the balloon has a distal end and includes a weakened portion near its distal end so that upon over inflation of the balloon the balloon will rupture near its distal end.

14. The balloon catheter of claim 1 wherein the balloon has a distal end and includes an wider distal portion so that upon over inflation of the balloon the balloon will rupture near its distal end.

15. The balloon catheter of claim 7 further including fairing means positionable proximally of the device for widening narrowed portions of the passageway to facilitate removal of the device from the passageway.

16. The balloon catheter of claim 15 wherein the fairing means comprises a fairing slidably carried about the device delivery shaft, the fairing tapering radially inwardly toward the proximal end of the fairing.

17. The balloon catheter of claim 16 further including a removal balloon catheter having an inwardly tapered distal end, the fairing including an internal surface configured and arranged to closely receive therein the distal end of the removal balloon catheter.

18. The balloon catheter of claim 16 wherein the fairing means includes stop means carried on the device delivery shaft for preventing the fairing from sliding proximally of the stop means.

19. A balloon catheter for introducing a device into a bodily passageway, the device having a predetermined maximum cross-sectional diameter, comprising:

an elongated inflatable balloon having proximal and distal ends, the balloon having a cross-sectional diameter, when deflated, smaller than the maximum cross-sectional diameter of the device being introduced into the passageway, the balloon being inflatable to define an inflated balloon cavity having a cross-sectional diameter along substantially its entire length larger than the maximum cross-sectional diameter of such device;

a balloon shaft having proximal and distal ends, the distal end of the shaft being removably attached to the distal end of the balloon;

a guidewire extending distally from the balloon's distal end;

an introduction chamber having proximal and distal ends, the chamber's distal end being attached to the proximal end of the balloon and being in direct communication with the balloon cavity so that, when the balloon is inflated, the device being introduced into the passageway can be advanced from the chamber into the inflated balloon cavity, the chamber including a shaft port through which the balloon shaft may be at least partially withdrawn;

a device delivery shaft having a distal end to which the device to be inserted may be mounted, the introduction chamber including a delivery shaft port through which at least a portion of the delivery shaft may be advanced; and inflation means in fluid communication with the balloon for inflating the balloon once the balloon has been inserted into the bodily passageway to allow introduction of the device into the passageway, the inflation means comprising a syringe in fluid communication with the balloon, the syringe including a plunger for exerting pressure on teh fluid to inject it into the balloon;

the balloon having a portion near its distal end configured so that upon over-inflation of the balloon the balloon will rupture near its distal end to free the device from the balloon.

20. A method for introducing a device into a bodily passageway, the device having a predetermined maximum cross-sectional diameter, comprising:

inserting into the passageway at least a distal portion of an elongated uninflated balloon catheter having a cross-sectional diameter, when deflated, smaller than the maximum cross-sectional diameter of the device being introduced into the passageway, the balloon catheter including a proximal introduction chamber attached to an end thereof for temporarily housing at least a portion of the device to be introduced into the passageway;

inflating the balloon along substantially its entire length to define a balloon cavity having a cross-sectional diameter larger than the maximum cross-sectional diameter of the device being introduced into the passageway; and advancing the device from the introduction chamber into the distal portion of the balloon cavity that is in the passageway.

21. The method of claim 20 further comprising the step of rupturing the balloon after the device has been advanced into the distal portion of the ballocn to free the device from the balloon.

22. The method of claim 21 further comprising the step of removing the balloon catheter after the balloon has been ruptured.

23. The method of claim 20 including the step of selecting the size of the balloon to have a diameter when inflated substantially egual to or larger than the diameter of at least a portion of the passageway through which the balloon is to be inserted.

24. The method of claim 20 wherein the inserting step further includes the step of advancing the distal end of the balloon catheter into the passageway until it reaches an widened portion of the passageway having a diameter larger than the normal inflated diameter of the balloon.

25. The method of claim 20 wherein the inserting step includes inserting the distal portion of the balloon catheter into a blood vessel and advancing the balloon catheter toward the heart until the distal portion of the balloon is in a wider portion of the vessel.

26. The method of claim 25 wherein the vessel into which the balloon catheter is inserted is the femoral artery, and the wider portion of the vessel, into which the distal portion of the balloon catheter is advanced, is the aorta.

27. The method of claim 20 wherein the advancing step comprises advancing a distal end portion of a cannula into the distal portion of the balloon that is in the passageway.

28. The method of claim 27 futher including the step of rupturing the balloon after the cannula has been advanced.

29. The method of claim 28 including the step of injecting fluid into the balloon after it has been ruptured and then repositioning the cannula within the balloon.

30. The method of claim 28 including the step of injecting fluid into the balloon after it has been ruptured and then substantially withdrawing the cannula from the portion of the balloon that is in the bodily passageway.

31. The method of claim 30 including the subsequent step of withdrawing the balloon catheter from the bodily passageway.

32. A method for introducing a device into a bodily passageway, the device having a predetermined maximum cross-sectional diameter, comprising:
   providing an uninflated, elongated balloon catheter having a proximal introduction chamber attached to an end thereof for temporarily housing the device to be introduced into the passageway, and selecting the size of the balloon to have a diameter when uninflated smaller than the maximum cross-sectional diameter of the device being introduced into the bodily passageway, and a diameter when inflated larger than the maximum diameter of such device and substantially equal to or larger than the inner diameter of at least a portion of the passageway through which the balloon is to be inserted;
   inserting into the passageway at least a distal portion of the uninflated balloon and advancing the distal end of the balloon into the passageway until it reaches a widened portion of the passageway having a diameter larger than the normal inflated diameter of the balloon;
   inflating the balloon to a diameter larger than the maximum cross-sectional diameter of the device being introduced into the bodily passageway, the inflated balloon defining a balloon cavity;
   advancing the device from the introduction chamber into the distal portion of the balloon cavity that is in the passageway;
   rupturing the balloon after the device has been advanced into the distal portion of the balloon cavity to free the device from the balloon; and
   removing the balloon after it has been ruptured.

* * * * *